(12) United States Patent  
LeBlanc et al.

(10) Patent No.: US 7,800,749 B2  
(45) Date of Patent: Sep. 21, 2010

(54) INSPECTION TECHNIQUE FOR TRANSPARENT SUBSTRATES

(75) Inventors: Philip Robert LeBlanc, Corning, NY (US); Douglas S Goodman, Pittsford, NY (US)

(73) Assignee: Corning Incorporated, Corning, NY (US)

( * ) Notice: Subject to any disclaimer, the term of this patent is extended or adjusted under 35 U.S.C. 154(b) by 653 days.

(21) Appl. No.: 11/809,091

(22) Filed: May 31, 2007

(65) Prior Publication Data

US 2008/0297784 A1    Dec. 4, 2008

(51) Int. Cl.  
*G01N 21/00*    (2006.01)

(52) U.S. Cl. ................ 356/239.1; 356/239.8; 356/495; 356/514

(58) Field of Classification Search ... 356/239.1–239.8, 356/73, 495, 511, 514, 497, 498  
See application file for complete search history.

(56) References Cited

U.S. PATENT DOCUMENTS

| 3,737,665 | A  | 6/1973  | Nagae .......................... 250/219 |
| 4,401,893 | A  | 8/1983  | Dehuysser ................... 250/572 |
| 5,459,330 | A  | 10/1995 | Venaille et al. ............. 250/559 |
| 5,517,301 | A  | 5/1996  | Dave .......................... 356/239 |
| 5,598,262 | A  | 1/1997  | Jutard et al. ................. 356/239 |
| 6,388,745 | B2* | 5/2002  | Stevens et al. ........... 356/239.7 |
| 6,633,377 | B1 | 10/2003 | Weiss et al. ............. 356/239.1 |
| 7,307,714 | B2* | 12/2007 | Cyr et al. ................. 356/239.1 |
| 2009/0052021 | A1* | 2/2009 | Mogami et al. ............. 359/385 |

* cited by examiner

*Primary Examiner*—Gregory J Toatley, Jr.  
*Assistant Examiner*—Iyabo S Alli  
(74) *Attorney, Agent, or Firm*—Robert P. Santandrea

(57) ABSTRACT

A method for inspecting a transparent substrate provides an index-matching fluid between an index-matched optical coupler and a surface of the transparent substrate. The method repeats, at two or more positions along the surface of the transparent substrate, steps of illuminating an inspection volume within the transparent substrate by directing a ribbon of light through the optical coupler and into the transparent substrate and detecting scattered light from the inspection volume at a detector that is optically conjugate with the inspection volume.

42 Claims, 23 Drawing Sheets

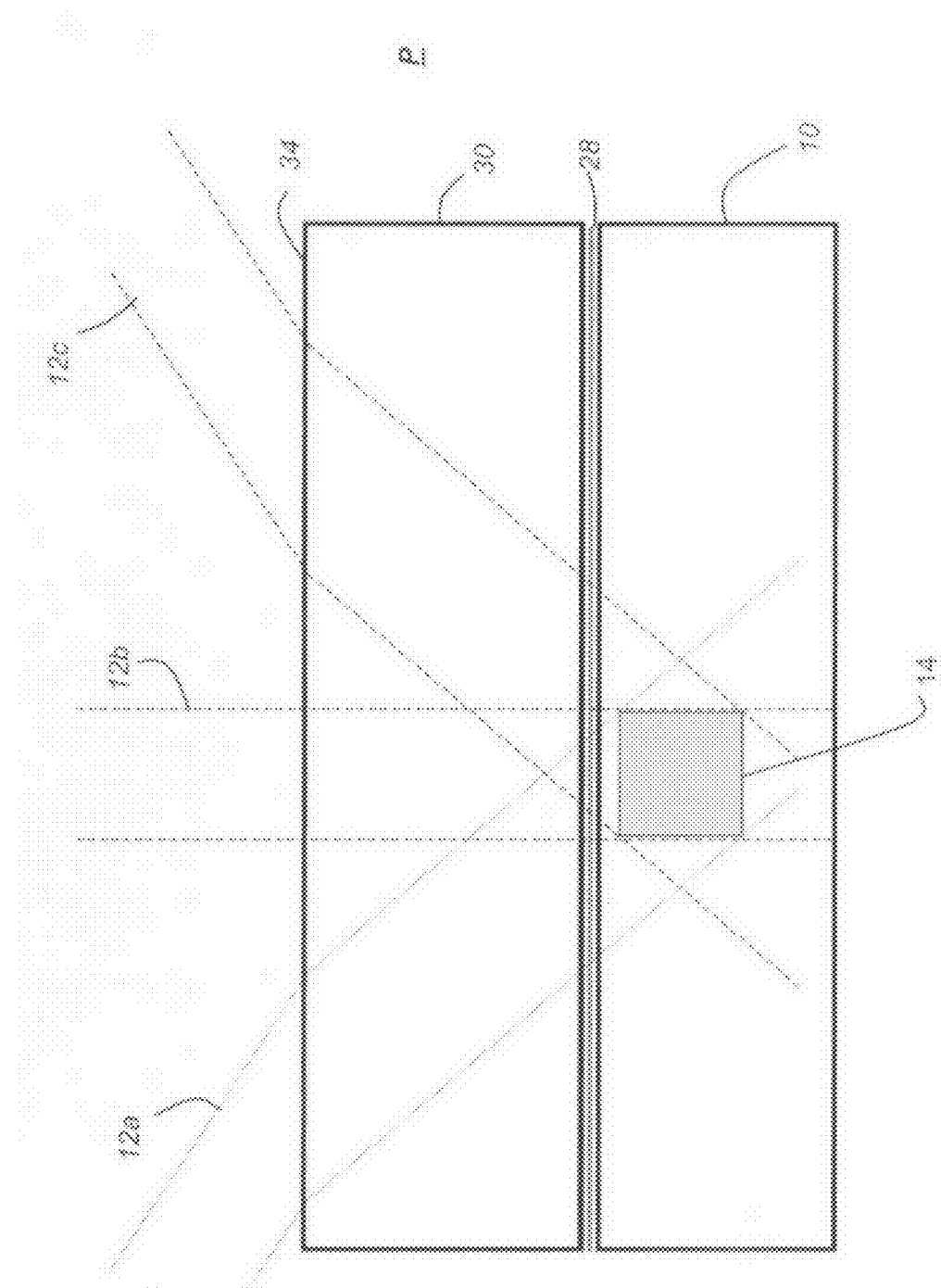

INSPECTION TECHNIQUE FOR TRANSPARENT SUBSTRATES

FIELD OF THE INVENTION

This invention generally relates to inspection methods for transparent substrates and more particularly relates to a method and apparatus for scanning the volume within an unpolished substrate to detect inclusions in glass and other transparent materials.

BACKGROUND OF THE INVENTION

In the manufacture of glass and other transparent substrates, it is often necessary to inspect the body of the transparent solid material for defects. In particular, detecting small inclusions that lie within the volume of the glass, where the inclusions are of micron or even submicron order, presents a considerable challenge. Inclusions within a glass medium can generally be classified in two groups: solid inclusions, which are formed by bits of unmelted or foreign material; and void inclusions, commonly formed by bubbles of gas. Solid inclusions can be formed by minute impurities in the starting materials which have been fused to form a glass; by bits of refractory material from the walls of the vessel in which the glass is prepared; or by impurities that are otherwise introduced during glass manufacture. The solid inclusions may be opaque or clear. Void inclusions, or gas bubbles, also present difficulties in visual inspection.

Inclusions can be particularly troublesome for high-purity glass materials such as those that serve as substrates for microlithography exposure masks and photomasks, for example. Often fabricated using processes other than flow process techniques, such as by vapor deposition, glass materials of this type can be very expensive to produce. Costly and time-consuming finishing processes are often needed in order to provide a final product from a glass boule manufactured in this way.

An inclusion inspection system that is suitable for high-value glass substrates of this type must meet the following performance criteria:
  (i) Sufficient speed. This requirement is of increasing importance as the relative size and volume of the glass substrate increases.
  (ii) Able to adapt to substrate thickness over a range.
  (iii) Good location specificity. The more accurately the location of an inclusion can be specified the better. When a defect location can be pinpointed, the affected area of the substrate can be removed from surrounding portions that pass inspection.
  (iv) Good sensitivity to inclusions. An inspection system for high-quality glass media should be able to detect micron- and sub-micron-level inclusions.
  (v) Insensitivity to surface quality. It is beneficial to detect inclusions within the volume of the glass as early as possible in the surface finishing cycle, before the surface is finely polished or otherwise treated to obtain an optical finish.

Where some of these requirements may work against each other, a reasonable balance must be achieved. For example, with reference to the criteria noted earlier, maximizing sensitivity (iv) could compromise speed (i) and robustness to surface quality (v). Conversely, maximizing speed (i) could have an adverse effect on both sensitivity (iv) and location specificity (iii).

Thus far, conventional inspection solutions for glass inclusions may meet one or two of these performance requirements, but fail to meet all five of these criteria. For example, manual inspection methods have been used and continue to be used for inclusion detection in a number of specialty glass manufacture environments. In order to use these methods, the glass surface is first polished to an optical finish. Then, high-intensity light wands are employed to painstakingly examine the inner volume of the glass. This method has a number of shortcomings. Speed (i) is a significant drawback. Another drawback is the requirement for a finished surface, as noted in criterion (v). There are limits on light types and intensities that are available, in consideration of operator safety. Further problems relate to high cost and relatively low repeatability.

Optical microscopy has also been used for detecting inclusions. Microscopy is characterized by an extremely narrow depth of field and a small sampling area at high magnification. While this solution is optimized for sensitivity, its slow speed (i) can be a significant drawback, making microscopy impractical for inspection of large volumes of bulk glass material.

Automated methods developed thus far for inclusion detection also have operational and performance drawbacks. Among proposed approaches for automated inclusion detection are techniques that employ Total Internal Reflection (TIR). TIR techniques use waveguide properties of the material under inspection. In practice, TIR methods are suitable only where the glass medium is relatively thin. These methods also require a highly finished surface and cannot be used effectively with thicker substrates, failing to meet the performance criteria identified earlier under items (ii), (iii) and (v). One illustrative example of this conventional method using TIR for a thin moving web of glass is described in U.S. Pat. No. 4,401,893 entitled "Method and Apparatus for Optically Inspecting a Moving Web of Glass" to Dehuysser. Another example for inspecting aircraft glass is given in U.S. Pat. No. 5,517,301 entitled "Apparatus for Characterizing an Optic" to Dave.

Side-lighting is another conventional method that has been described for glass inspection. This method is hampered by unevenness in the illumination path and other problems such as the requirement for a finished surface, requirements for high-intensity sources, and some inherent diffraction at glass edges and scattering. A flat, polished edge is required for the incident light. With larger sized glass sheets, the bowing of longer sections can cause additional problems. As a result, this method is constrained to bodies of glass having limited length and width dimensions. Thus, side illumination techniques fail to meet inspection criteria (ii), (iv), and (v) listed earlier and are impractical for glass boules and where lengths of glass exceed about 20 inches. One example of a side-lighting technique is described in U.S. Pat. No. 3,737,665 entitled "Method and Apparatus for Automatically Detecting Defects and Irregularities in Glass Sheet" to Nagae.

Another approach has been to direct light into the substrate and to block all light detectable by a sensor except for the scattered light caused by inclusions. This type of approach is described, for example, in commonly assigned U.S. Pat. No. 6,388,745 entitled "Detecting Inclusions in Transparent Sheets" to Stevens et al. and in U.S. Pat. No. 6,633,377 entitled "Dark View Inspection System for Transparent Media" to Weiss et al. These approaches can detect inclusions above a certain size, but are not capable of providing accurate information on inclusion depth, thus fail to meet criteria (ii), (iii), (iv), and (v).

Yet another approach has been to direct a curtain of HeNe laser light into the glass surface, with one or more cameras poised at oblique angles for detecting scattered laser light from inclusions, as described in U.S. Pat. No. 5,459,330 entitled "Process and Device for the Inspection of Glass" to Venaille et al. This type of approach is not well-suited to rough surfaces and, because it is prone to generating secondary scattering from the top surface, fails to meet the requirements given earlier as criterion (ii), making it difficult to isolate true inclusions from surface defects. It also fails to meet sensitivity requirements (iv). Where there is surface curvature, the resulting refraction can make it difficult to completely scan the full volume of a glass substrate without gaps. Where both top and bottom surfaces have curvature, multiple reflections can occur within the field of view of sensing optics. In summary, methods such as those described in the Venaille et al. '330 disclosure fail to meet criteria (i), (ii), (iv), and (v) for inclusion inspection systems for high-value glass.

All of the techniques noted earlier suffer from the same significant limitation: failing to meet criterion (v). That is, each of these conventional techniques requires a highly finished, optical quality surface. This means that the glass must be fully cycled through the manufacturing process before it can be tested for inclusions. It can be appreciated that this entails additional expense and represents wasted effort in some cases, since an inclusion can render the glass sheet, or some portion of the glass medium, useless for its intended application and this defect cannot be found until a significant amount of value-added manufacturing has been applied to the glass substrate.

As noted earlier, other related shortcomings of conventional approaches include disappointing performance due to problems such as light loss, intensity variation, and dimensional limitations, particularly acute with methods using TIR and side-lighting methods, such as those cited. Conventional approaches have been developed and used for glass having surfaces that are in a relatively finished state, such as glass fabricated by flow processes, but do not satisfy the more demanding requirements of inspection for high-quality glass formed using deposition or other alternative processes for which a sequence of finishing and polishing procedures may be needed in order to properly condition the surface.

With respect to performance criteria (i) through (v) listed earlier, conventional approaches have proved to be deficient in at least one or more of these requirements. Thus, it can be appreciated that there is a need for a glass inspection method and apparatus that allows accurate inspection of the bulk or internal volume of a glass substrate medium that provides sufficient speed, that does not require a highly finished surface and is not constrained to thin sheets of glass, that identifies the location of inclusions at specific locations, and that exhibits sufficient sensitivity for detecting very small inclusions.

SUMMARY OF THE INVENTION

It is an object of the present invention to advance the art of glass inspection. With this object in mind, the present invention provides a method for inspecting a transparent substrate comprising:

a) providing an index-matching fluid between an index-matched optical coupler and a surface of the transparent substrate; and b) repeating the following steps at two or more positions along the surface of the transparent substrate:

(i) illuminating an inspection volume within the transparent substrate by directing a ribbon of light through the optical coupler and into the transparent substrate; and (ii) detecting scattered light from the inspection volume at a detector that is optically conjugate with the inspection volume.

It is a feature of the present invention that it uses an index-matched optical component for directing illumination into the substrate and for obtaining an image that can be analyzed to reveal light scattering by an inclusion.

It is an advantage of the present invention that it allows inspection of the bulk of a transparent medium without requiring that the surface of the medium be finished. The method and apparatus of the present invention allow inspection for inclusions in bulk substrate of variable widths and sizes, before surface processing is completed.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 8C is a plan view of the plane of illumination used in the embodiment of FIG. 8A.

DETAILED DESCRIPTION OF THE INVENTION

Figure 1A:
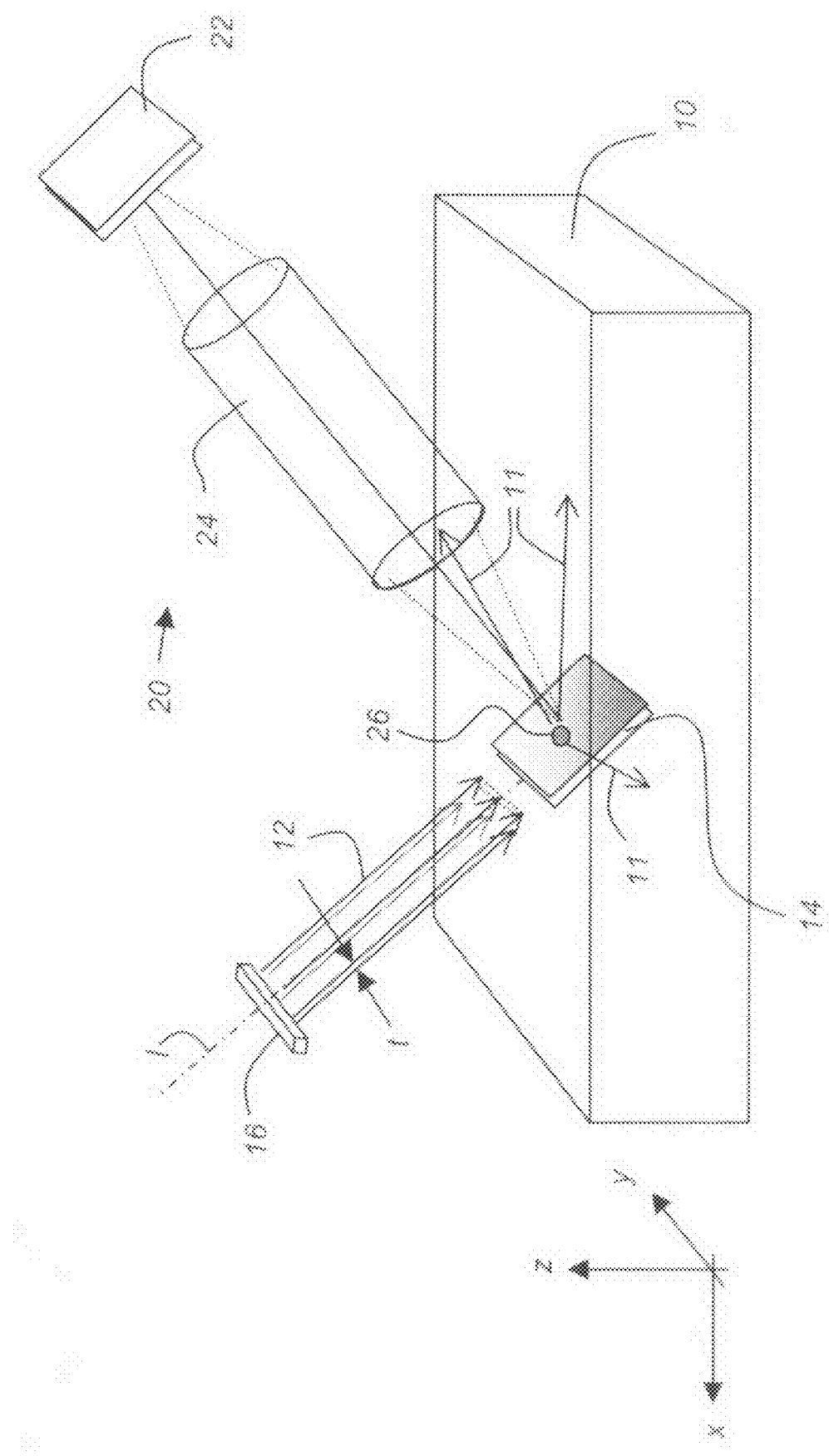
FIG. 1A is a perspective view showing how an inspection volume is formed and detected using the method of the present invention.

In the context of the present disclosure, terms "top" and "bottom" are relative and do not indicate any necessary orientation of a surface, but may be used simply to refer to and distinguish opposite surfaces for a component or block of transparent material. Throughout this disclosure, the terms "substrate", "medium", or "material" may be used interchangeably to identify the solid, transparent material, such as glass, that is being inspected.

Figures shown and described herein are provided in order to illustrate key principles of operation and component relationships along their respective optical paths according to the present invention and are not drawn with intent to show actual size or scale. Some exaggeration may be necessary in order to emphasize basic structural relationships or principles of operation. Some conventional components that would be needed for implementation of the described embodiments, such as actuators, optical mounts, or necessary support structures, for example, are not shown in the drawings in order to concentrate description on the invention itself.

In the context of the present disclosure, the term "oblique angle" has its conventional meaning, as either greater than or less than a right (90 degree) angle and not parallel with respect to its reference.

The terms finished and unfinished, as applied to glass or other transparent substrate, refer to relative states of specialty glass, as described earlier in the background section, that are seldom fabricated in a flow process, but rather, are formed as boules using various techniques such as deposition, well known to those skilled in the glass fabrication arts. In finish processing, the glass boules are sliced, then typically ground and polished in successive stages until a body of glass substrate having an optical surface is formed. As was noted earlier, conventional glass inspection techniques require that the glass have an optical finish as a prerequisite to inspection for inclusions. The apparatus and method of the present invention, however, can be used for glass having a surface that is relatively unfinished, such as in its boule stages or when polished to as rough as 120 grit or finer.

The term "optical contact" is conventionally used by those skilled in the optical arts to describe a condition of optical continuity between two surfaces, forming, with respect to light traveling through both surfaces, a single "monolithic" optical element from two or more elements and the bridging material between them. In conventional parlance, there is optical contact between two surfaces where there is either direct surface contact at the interface or where a transparent bridging fluid at the interface effectively eliminates refraction, absorption, reflection or other unwanted optical effects at the interface, or reduces these to a negligible level. For some types of optical components, an optical adhesive serves as this bridging fluid. However, this bridging fluid need not have adhesive properties, but can also be an index-matching liquid, having a range of possible viscosities, including oil or gel substances, for example. As used in the context of the present disclosure, this transparent bridging fluid, index-matched with respect to the optical components at the interface, can have a variable depth and still provide optical contact that meets this requirement for optical continuity. As can be appreciated by those skilled in the optical arts, the depth of index-matching fluid that bridges the two surfaces can vary and still maintain optical contact.

Two principal illumination approaches have been employed for various techniques that detect a foreign particle that is positioned within a volume. Brightfield imaging directs illumination into the detecting optical system and measures the small amount of energy loss resulting from scattering or blocking of the light by the particle. However, the small reduction in returned energy resulting from the small particle often makes the small particle or other inclusion difficult to detect. Further, the small reduction in energy from small particles or other inclusions can be effectively masked by variations in the bright surrounding background. As a result, inclusions can be difficult or impossible to detect without numerous false detections when using brightfield illumination.

The alternate approach, darkfield imaging, widely used in microscopy and other fields, uses oblique illumination, directed at an angle that is away from the detecting optical system. A darkfield imaging apparatus obtains an image from light that is scattered or diffracted by the particle within its object plane. In general, darkfield illumination is more sensitive than its brightfield counterpart, because it provides high contrast from the scattering particle or other inclusion, yielding a high signal-to-noise ratio. This allows improved sensitivity at lower magnification, permitting faster inspections for limit size defects. Darkfield imaging also more readily renders itself to Fourier filtering and other techniques for enhancing signal to noise ratios.

The method of the present invention can be applied for use with either brightfield or darkfield illumination. For the purpose of description, this disclosure primarily shows and describes various embodiments using darkfield illumination. However, it can be appreciated by those skilled in the optical design arts that alternative brightfield illumination techniques could also be used for many of these embodiments, with the corresponding changes made to the orientation of the illumination and detection optics.

The method and apparatus of the present invention are directed to inspection of the bulk of a glass or other transparent substrate medium, rather than to inspection of its surface. Unlike conventional inclusion detection approaches that require the glass medium to have a finished surface, the present invention allows the surface to be unfinished, without foreign matter. Thus, the present invention advantageously allows inclusion inspection at an earlier stage of glass processing than was previously possible, prior to the final stages that include surface finishing.

Figure 1B:
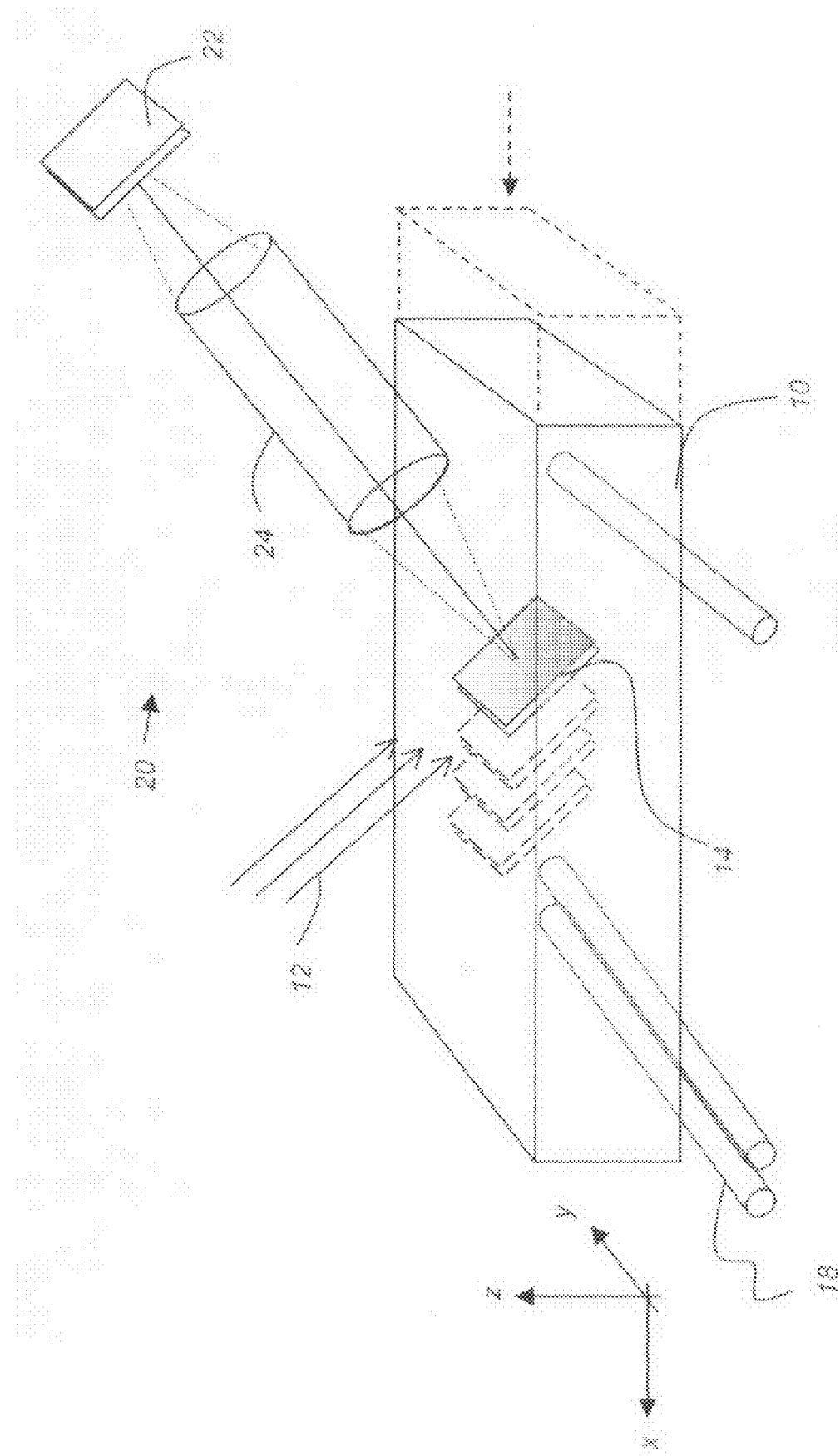
FIG. 1B is a perspective view showing scanning of the inspection volume in a direction along the x-axis.
Figure 1C:
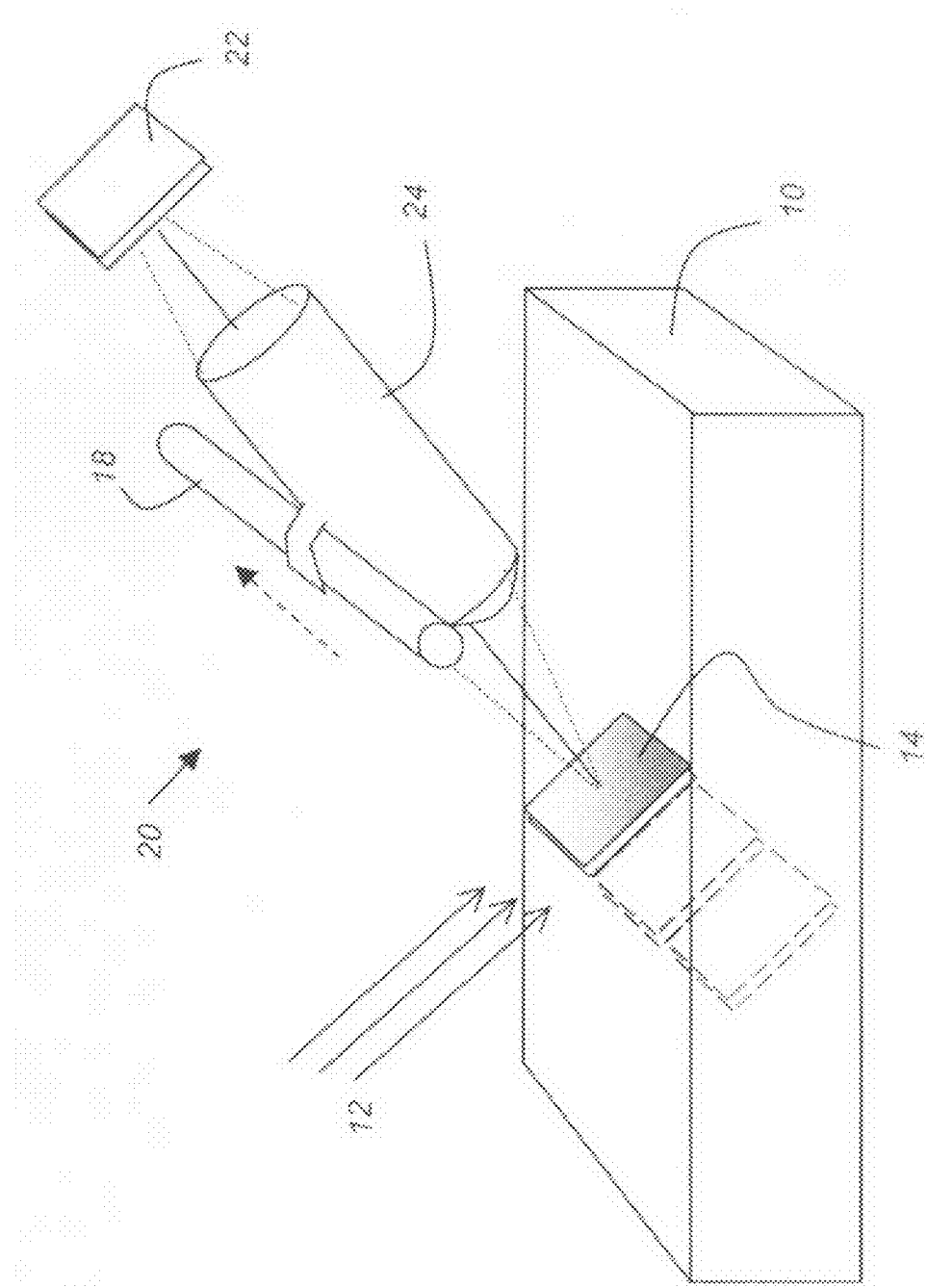
FIG. 1C is a perspective view showing scanning of the inspection volume in a direction along the y-axis.

FIGS. 1A, 1B, and 1C show, in simplified form and ignoring refraction for the moment, the basic principle of the present invention that is used by each of the embodiments that will be described subsequently. The inner volume or bulk of a transparent substrate 10, such as glass, is to be inspected for inclusions. The surface of the glass may be rough or unfinished and may even exhibit some sub-surface micro-cracks. A ribbon-shaped beam of light, ribbon of light 12, is directed from a light source 16 into transparent substrate 10. A detector apparatus 20 has a detector 22 and an optical system for directing light, shown as a light director 24. Typically, light director 24 has two or more lenses, but may have any of a number of possible arrangements of optical components, as described subsequently in more detail.

Ribbon of light 12, having some thickness t, illuminates a corresponding ribbon-shaped illumination region within the body of substrate 10. Ribbon of light 12 is directed along a primary illumination axis I, where axis I is parallel to the x-z plane using the axes assignments shown. The intersection of this illumination region and a detection volume of detector apparatus 20, corresponding to the field of view of detector apparatus 20, forms an inspection volume 14. In an axially symmetric optical system, such as that represented in FIGS. 1A-1C, light director 24 is positioned so that inspection volume 14 is at one focal plane and detector 22 is at its conjugate focal plane. Thus, with this arrangement, light director 24 images inspection volume 14 onto detector 22. This would allow detector 22 to be a CCD (charge-coupled device) or CMOS (complementary metal-oxide semiconductor) detector array or camera device, for example. In a more general case, light director 24 need not be axially symmetric, but, more broadly stated, directs light from inspection volume 14 to detector 22. By means of light director 24, inspection volume 14 is conjugate to detector 22. Thus, instead of providing an imaging array, detector 22 could be one or more photodiodes or other type of discrete sensors. Detector 22 can be connected to any of a variety of types of systems that display an image from inspection volume 14 or that analyze the obtained data from scattered light, such as a machine-vision system, familiar to those skilled in the inspection arts.

As represented in FIG. 1A, inspection volume 14 typically occupies only a small portion of the overall volume of transparent substrate 10. An inclusion 26 within inspection volume 14 tends to scatter light, indicated as scattered light 11, some portion of which may be directed to and sensed by detector 22. In order to inspect the full volume of transparent substrate 10, the method of the present invention translates or scans inspection volume 14, along with its corresponding detection components, in one or more directions through the transparent medium. As shown in FIG. 1B, a transport apparatus 18 provides the relative motion between transparent substrate 10 and detector apparatus 20 that is needed for scanning the bulk volume. In the example of FIG. 1B, transport apparatus 18 moves transparent substrate 10 to the left, effectively translating inspection volume 14 through the transparent medium in the rightward direction. Using the coordinate axes assignments shown in FIG. 1B, this movement provides scanning in the direction of the x-axis. As FIG. 1C shows, scanning in the y-axis direction is also possible with this arrangement.

It can be appreciated by those skilled in the optical arts that scanning can be effected using any of a number of different, well-known transport mechanisms and techniques. FIG. 1B suggests rollers or a belt-driven actuator that is actuable for providing scanning in the x-direction, for example. FIG. 1C suggests a leadscrew or other mechanism that is actuable for scanning detector apparatus 20 in the y-direction. Clearly, transport apparatus 18 could operate by scanning detector apparatus 20 in both directions over a stationary body of transparent substrate 10. Alternately, detector apparatus 20 could be stationary, with transparent substrate 10 moved in various directions to effect scanning. As yet another alternative, transport apparatus could move both substrate 10 and detector apparatus 20 in order to effect this translation of inspection volume 14 and its corresponding detection components.

Scanning of transparent medium 10 can be continuous, so that transport apparatus 18 translates inspection volume 14 through the volume of the transparent substrate in smooth, continuous motion. Alternately, step-and-repeat methods could be used for inspection, requiring a corresponding movement pattern.

It is important to observe that scanning the volume of transparent substrate 10 in the manner shown in FIGS. 1A-1C as just described requires that components maintain respectively fixed positions, such as by being mechanically coupled, so that inspection volume 14 and its optically conjugate detector 22 effectively travel together, maintaining their positions and alignment relative to each other.

In the basic inspection and scanning sequence shown in FIGS. 1A-1C, then, inspection volume 14 is formed within the bulk of the material and light is directed from inspection volume 14 onto detector 22. Inspection volume 14 is translated to at least a second position, but more typically to a number of other positions within the substrate, and detector 22 is correspondingly shifted in location in order to receive light from inspection volume 14 in this second and in subsequent positions. This same sequence of operation can be implemented using a number of different embodiments, as is described subsequently, and provides methods for bulk inspection of the volume of a glass material, or other transparent bulk material, that do not require a finished surface.

Figure 2:
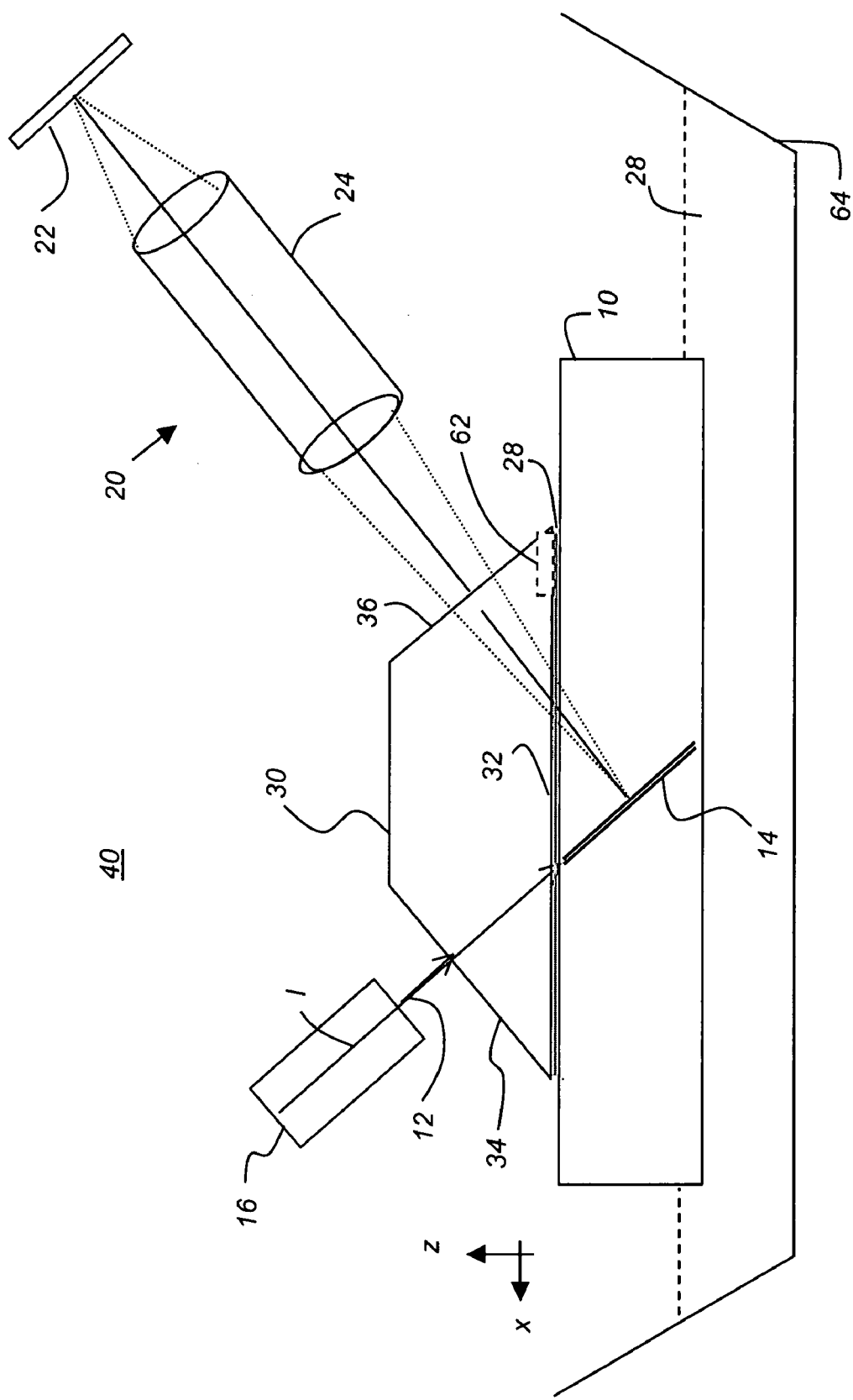
FIG. 2 is a cross-sectional schematic diagram showing components for scanning the volume of a transparent substrate in one embodiment.
Figure 3:
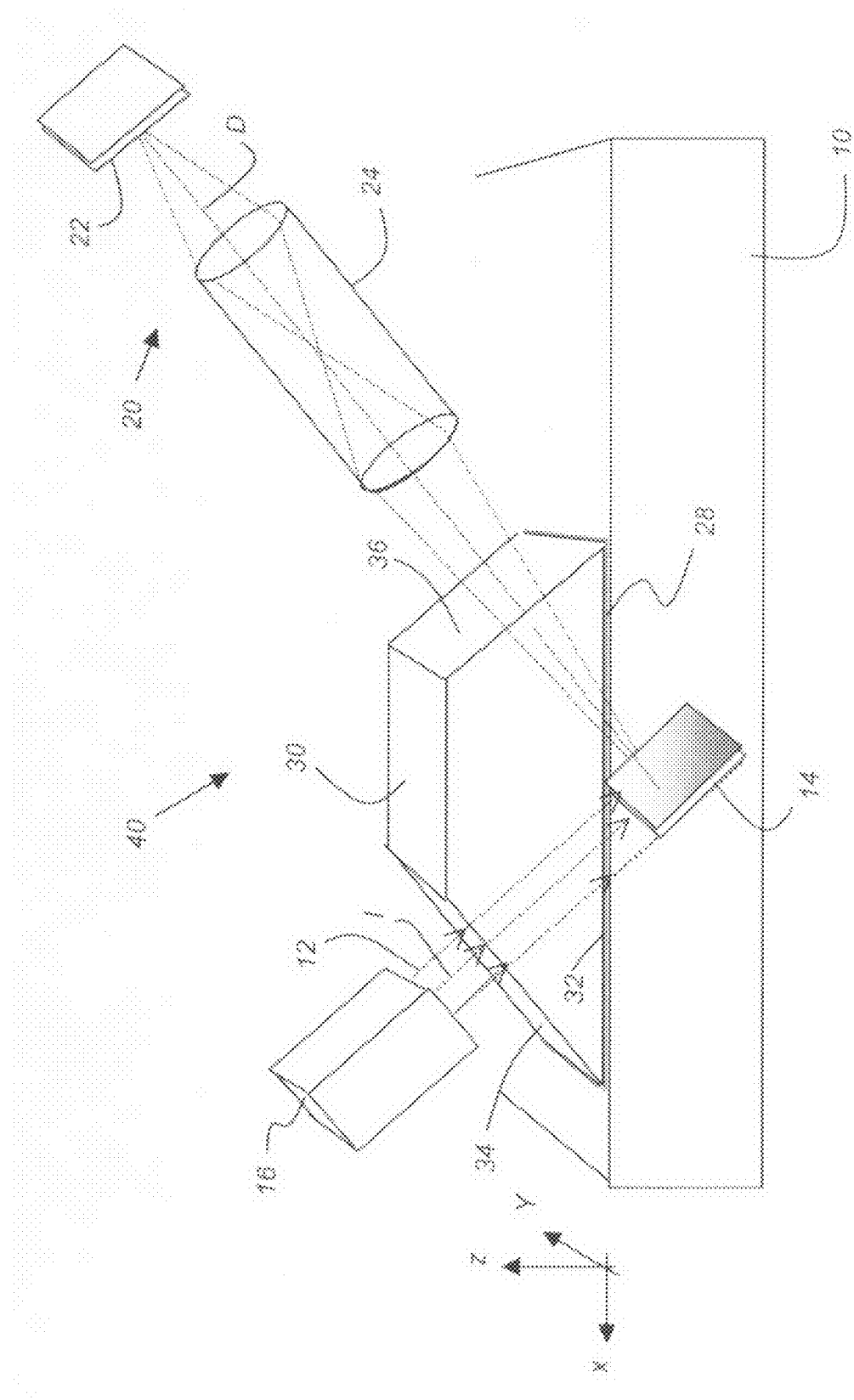
FIG. 3 is a perspective view showing inspection components in one embodiment.

As emphasized earlier, the description of FIGS. 1A-1C ignored refraction in order to more clearly illustrate the underlying method of the present invention. However, for any apparatus embodiment of the present invention, refraction cannot be ignored. Referring to FIG. 2, there is shown, in schematic and side-view form, an embodiment of the present invention that takes refraction into account. FIG. 3 shows optical components of this embodiment in perspective view. In an optical apparatus 40, light source 16 provides ribbon of light 12 along a principal illumination axis I through an index-matched coupler 30, shown as a prism in this and other embodiments. An index-matching fluid 28 lies between a bottom surface 32 of index-matched coupler 30 and the surface of transparent substrate 10, so that optical contact is provided between index-matched coupler 30 and substrate 10. Index matching fluid 28 can be, for example, an immersion oil. As shown in FIG. 2, there may also be index-matching fluid 28 in a tank or container 64 beneath transparent substrate 10. Typically, inner surfaces of container 64 have a light-absorptive coating to prevent unwanted reflection from light that passes through substrate 10. For simplicity, subsequent figures do not show container 64, but this arrangement may be used with any of the horizontal embodiments that are described.

Index-matched coupler 30 has an illumination surface 34 that is substantially normal to the principal axis I of ribbon of light 12. Index-matched coupler 30 also has a light directing surface 36 for directing the light path between inspection volume 14 and detector 22. Where detector apparatus 20 is radially symmetric, as shown in FIG. 3 with symmetry about a detector axis D, light-directing surface 36 is normal to detector axis D. However, other arrangements that are not radially symmetric can be used for directing light from index-matched coupler 30, as is described subsequently.

Index-matched coupler 30 may include features that absorb or block unwanted portions of scattered light for improved sensitivity. As shown in FIG. 2, for example, a light-absorptive feature 62 may be formed on surface 32 to block and absorb any stray light from light director 24. Index-matched coupler 30 may be the same type of glass as is used for substrate 10. If another material is used, it must exhibit the same index of refraction n at the wavelength or wavelengths used for illumination from light source 16.

Optical contact is provided between surfaces of index-matched coupler 30 and substrate 10 using index-matching fluid 28, such as fluids, oils, or transparent gels of the index-matching types manufactured by Cargille Laboratories, Inc., Cedar Grove, N.J.

Inspection volume 14 has been shown at an oblique angle relative to the surface of transparent substrate 10. While this oblique orientation is not required, it offers a number of advantages for detection of scattering. With a radially or axially symmetric imaging arrangement as shown in FIGS. 2 and 3, the oblique orientation of inspection volume 14 allows it to be positioned at a focal plane of light director 24 optics. Inspection volume 14 can then be imaged at detector 22. With inspection volume 14 and detector 22 in this optically conjugate relationship, a two-dimensional image of inspection volume 14 can be obtained. This is an advantageous arrangement when detector 22 is a camera or other imaging device using a CCD or CMOS imaging array. Note that the oblique angle need not be at 45 degrees; other angles may be advantageous.

Not shown in FIGS. 2, 3, or following, is any mechanical coupling arrangement that could be used for positioning and alignment of optical apparatus 40. That is, a bracket, support, or any of a number of other types of mounting arrangements may be used to mechanically couple components of optical apparatus 40; light source 16; index-matched coupler 30; and detector apparatus 20 components including light director 24 and detector 22, so that these components are aligned and travel together with respect to each other. Alternatives for mounting optical components of optical apparatus 40 are well-known in the opto-mechanical arts. The alternative mounting arrangement that is selected in any particular embodiment would depend, in part, on the type of transport apparatus 18 that is used, as was described earlier with reference to FIGS. 1B and 1C.

As the term implies, ribbon of light 12 is characterized as being elongated in a direction orthogonal to its incident direction, but fairly thin. In the perspective view of FIG. 1A, thickness dimension t indicates that ribbon of light 12 has some small thickness dimension t relative to the x-z plane, and is extended in the general direction of the y axis. In practice, thickness t should be dimensioned as slightly smaller than, or at least not exceeding, the depth of field of light detector 24. Excessive thickness would not be desirable, since it could result in scattering from inclusions that lie outside inspection volume 14.

There are a number of techniques for forming ribbon of light 12 from a variety of light sources. Light source 16 could include a laser that scans in a predetermined pattern or a laser that has its beam reshaped when it is directed through one or more cylindrical lenses. As another alternative practiced by those skilled in the laser illumination arts, a holographic diffuser could be used in combination with a cylindrical lens. Non-laser sources could also be used, with appropriate optics for forming ribbon of light 12. For example, LEDs or strobed light sources or lamps, including filament-based lamps of some type, such as incandescent lamps, could be used to generate this illumination. Unlike conventional embodiments for glass inspection, such as embodiments described earlier in the background section, the inspection method and apparatus of the present invention are not wavelength-limited. The light can be monochromatic or broadband, visible, or outside the visible range. It is important to note that the index-matching condition obtained using index-matching fluid 28 must correspond to the wavelength(s) used.

Collimated light is advantaged but is not required for forming ribbon of light 12. Collimated light provides a well-defined inspection volume and helps to minimize the unwanted effects of stray light within the bulk of the glass or other transparent medium. Ribbon of light 12 could also extend lengthwise, in the y-direction using the axis assignments of FIGS. 1A-1C, and could exceed the field of view of light director 24 optics in this direction. In one embodiment, ribbon of light 12, in the direction of the principal illumination axis, extends fully across the length of transparent substrate 10, so that detector apparatus 20 effectively defines inspection volume 14 as that portion of ribbon of light 12 that is within its field of view as it scans along in the y direction. With this embodiment, it can be challenging to provide collimated light, with its advantages as just noted, or to compensate for problems with stray light. In such an embodiment, light source 16 would be mechanically coupled for scanning along with detector apparatus 20 components in the x-axis direction.

For embodiments described thus far, all of the components of optical apparatus 40 are on the same side of transparent substrate 10. While this arrangement can be advantageous in some applications, however, it is not required; some of the embodiments of optical apparatus 40, described subsequently, have components on opposite sides of transparent substrate 10.

One important aspect of the present invention relates to index matching. Both optical coupler 30 and index-matching fluid 28 have the same refractive index n of transparent substrate 10. At a glance, it can be readily appreciated by those skilled in the optical arts that index-matching with the arrangement of FIGS. 2 and 3 minimizes or eliminates problems such as reflection or refraction that would otherwise be caused at the interfaces between components along the illumination and detection optical paths shown. Light at normal incidence would not experience refraction at surfaces 34 or 36.

Index-matching using index-matching fluid 28 has advantages in acting as a lubricant for scanning index-matched coupler 30 along the surface of transparent substrate 10. In addition, the use of index matching fluid 28 also helps to compensate for some amount of roughness in the unfinished substrate surface. A pool of index-matching fluid 28 could be provided over the full surface of transparent substrate 10 or, alternately, index-matching fluid 28 could be provided from an optional supply that is also coupled to optical apparatus 40.

Figure 4:
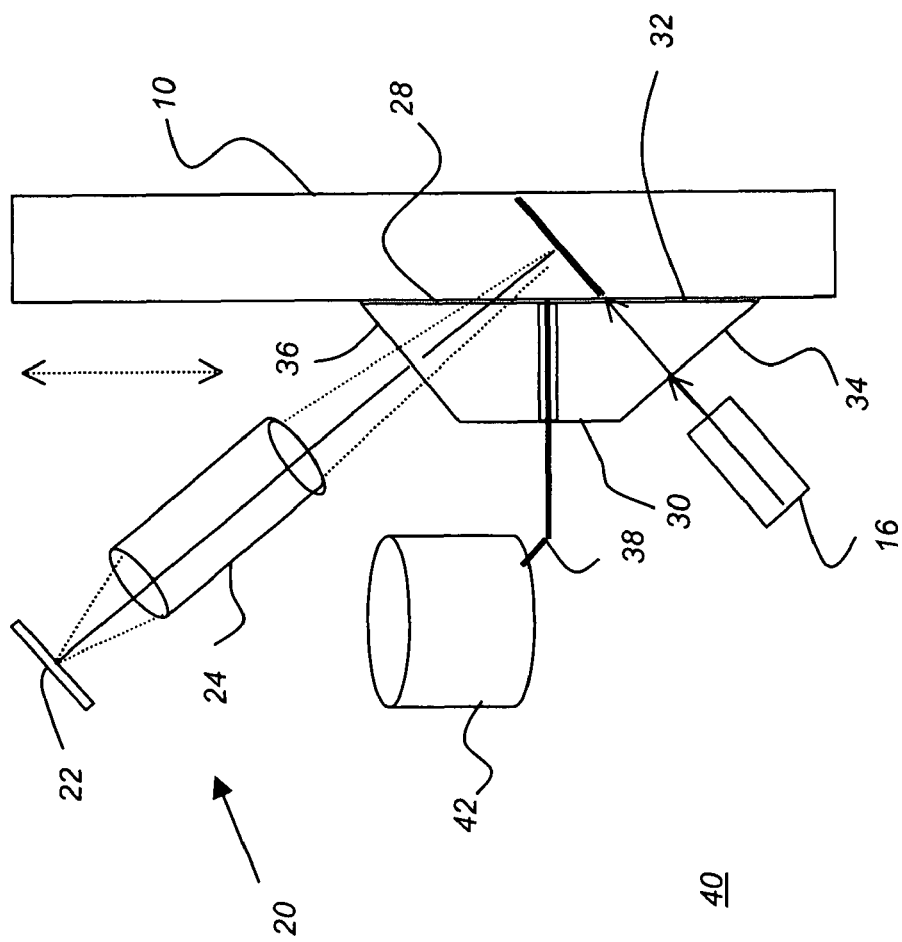
FIG. 4 is a side view of an inspection apparatus in a vertical orientation.

The side view of FIG. 4 shows an embodiment of optical apparatus 40 in a vertical orientation. This embodiment also includes a fluid source 42 and tubing or other conduit 38 for supplying index-matching fluid 28 needed to provide optical contact between index-matched coupler 30 and transparent substrate 10. Here, index-matching fluid 28 is provided through an orifice in index-matched coupler 30. Other configurations could alternately be used.

Figure 5:
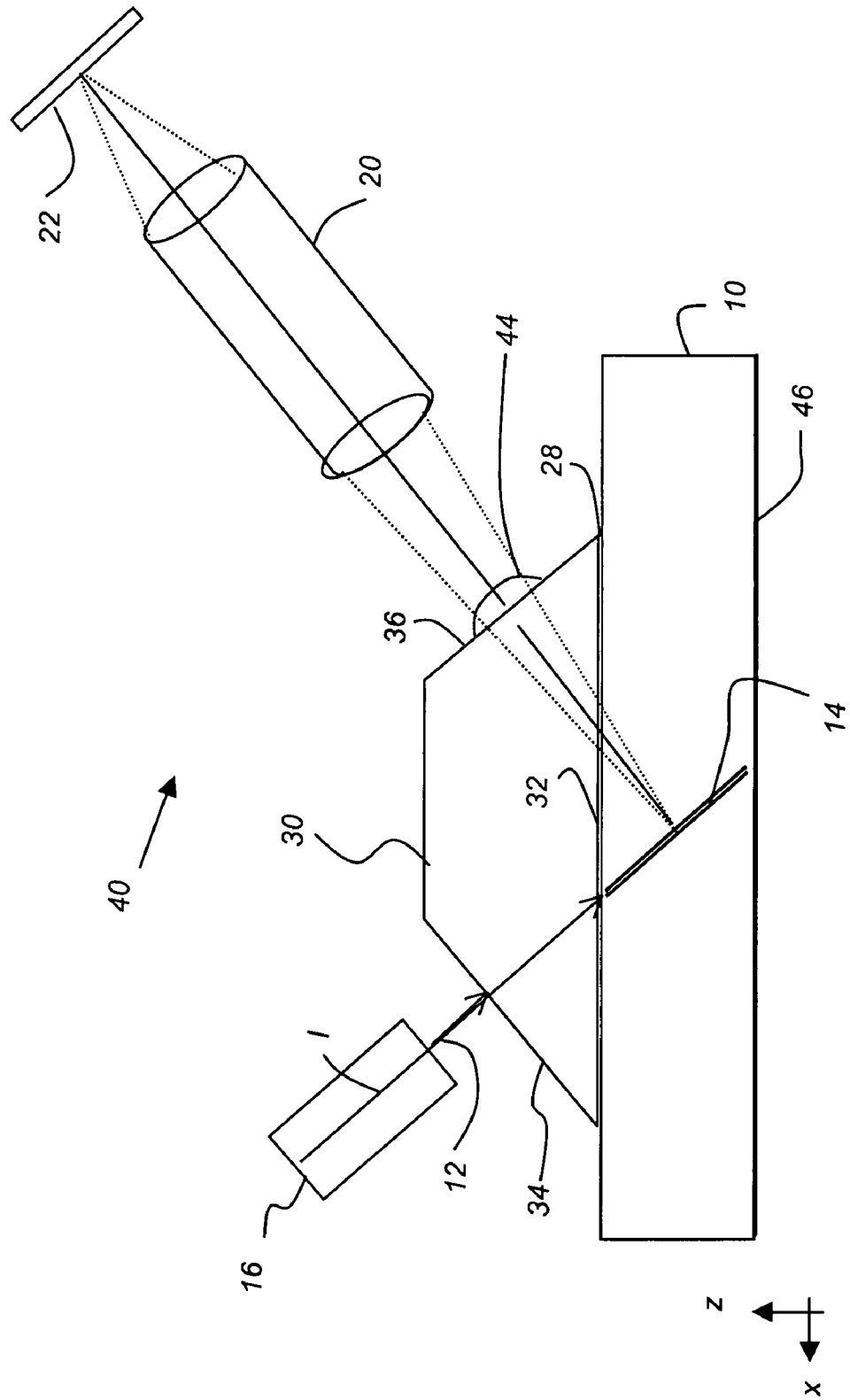
FIG. 5 is a cross-sectional schematic diagram showing components for scanning the volume of a transparent substrate in which a lens is added to the light redirecting output surface of the coupling prism in one embodiment.

A number of different types of supporting optical components can be provided to improve system operation or to fine-tune performance for various conditions. One example is shown in FIG. 5. Here, a lens 44 or, more generally, a refractive structure or element, is attached to or formed over some portion of, or all of, light-directing surface 36. Lens 44 may help, for example, by providing telecentricity along the detection optical path. Double telecentricity would be advantageous for providing improved imaging. It should also be noted that surface 34 could also have some curvature or otherwise be treated to condition the illumination path.

Polarization properties of inclusions can also be used for enhancing sensitivity. For this purpose, light source 16 could provide polarized light. Polarization films and other components could then be used for managing and using polarized light in the detection optics. For example, polarized light having one polarization state could be provided by light source 16, with polarization of the orthogonal state, indicating scattering within inspection volume 14, detected at detector 22. A polarizer and analyzer in combination could be used for providing and detecting polarized light, using techniques known to those skilled in the optical arts.

Figure 6:
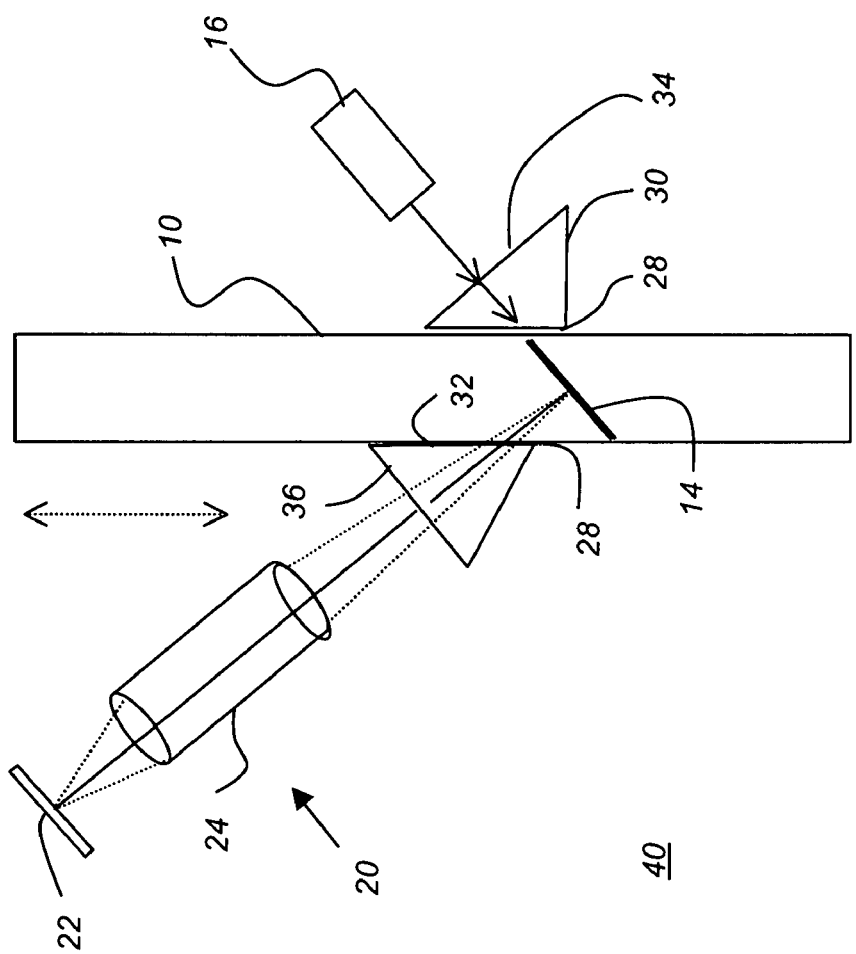
FIG. 6 is a side view of an inspection apparatus with illumination and detection components on opposite sides of the substrate.

There are a number of options for providing illumination. Ribbon of light 12 can be provided from the same side of transparent substrate 10 or from the opposite side. Referring to FIG. 6, there is shown an embodiment that has the detector optical components and illumination components on opposite sides of transparent substrate 10. There is an index-matched coupler 30 on each side of transparent substrate 10 and mechanical coupling is maintained between detector optical components and illumination components. Index-matching fluid 28 is used between the surfaces of substrate 10 and the corresponding facing surfaces of each optical coupler 30.

Stray light from reflection against either surface of transparent substrate 10 can create unwanted effects and false readings. In order to reduce stray light to negligible levels, a light-absorbent coating 46 or other treatment can be added to the opposite surface of substrate 10. Light-absorbent treatments could include paint or other deposited materials, for example.

As described earlier, inspection volume 14 has some thickness, thus can be said to occupy some volume within transparent substrate 10, as a factor of light dispersion within the substrate. For improved reading efficiency and accuracy, the depth of field of each light director 24 should approximate the thickness of inspection volume 14.

Figure 7:
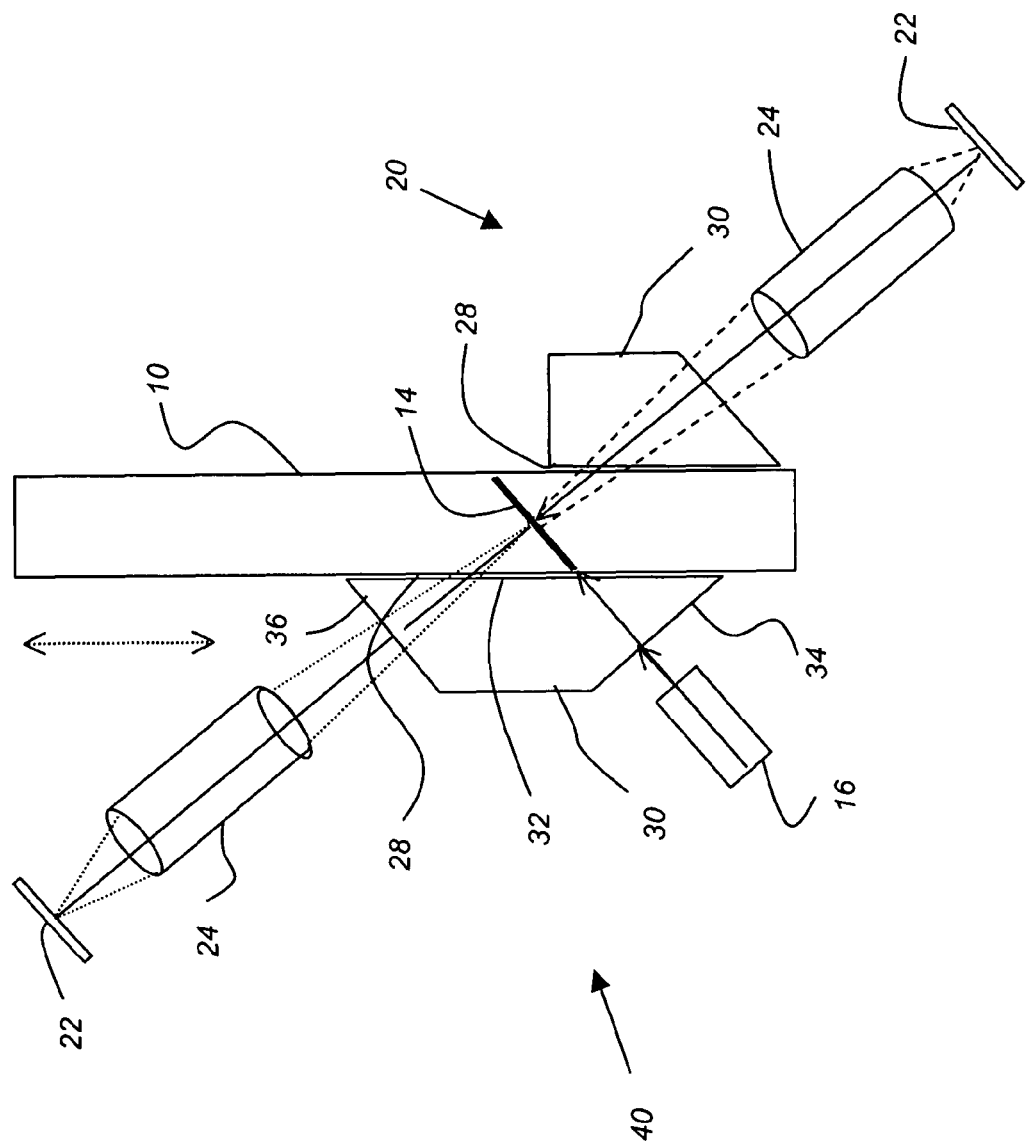
FIG. 7 is a side view of an inspection apparatus showing multiple light directors and detectors in one embodiment.

Improved detection sensitivity may be obtained in a number of ways. In the embodiment shown in the side view of FIG. 7, two detectors 22 are used in detector apparatus 20, one on each side of transparent substrate 10. Similarly, a configuration with two or more illumination paths could also be used. This could also help to increase speed of measurement as well as to provide improved surface discrimination and sensitivity with the benefits of coincident detection. In another embodiment using two detector apparatus 20, each detector apparatus 20 could be aligned to detect light along a different depth of substrate 10.

Figure 8A:
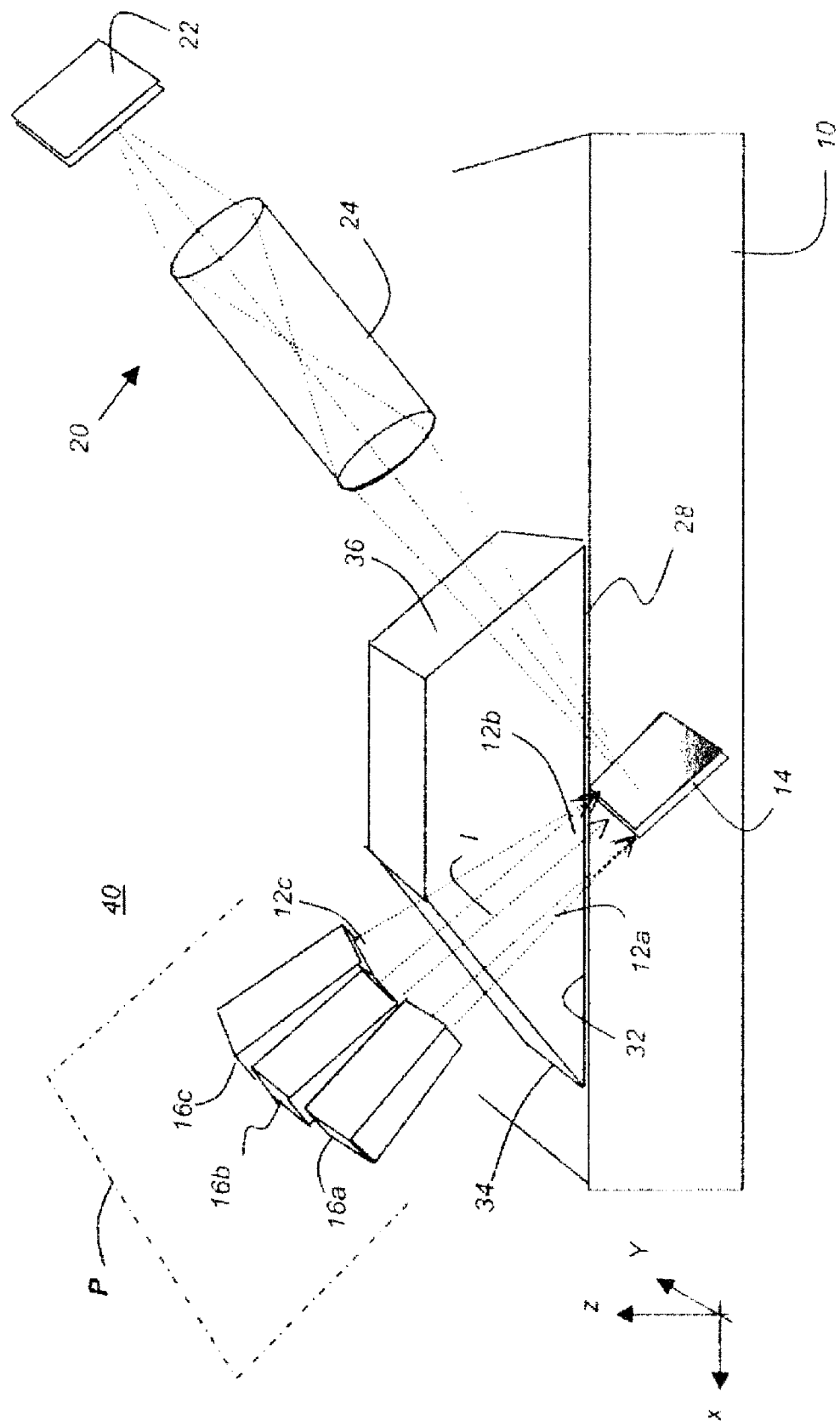
FIG. 8A is a perspective view of an embodiment that uses multiple light sources fanned out at slightly different angles, but within the same plane.
Figure 8B:
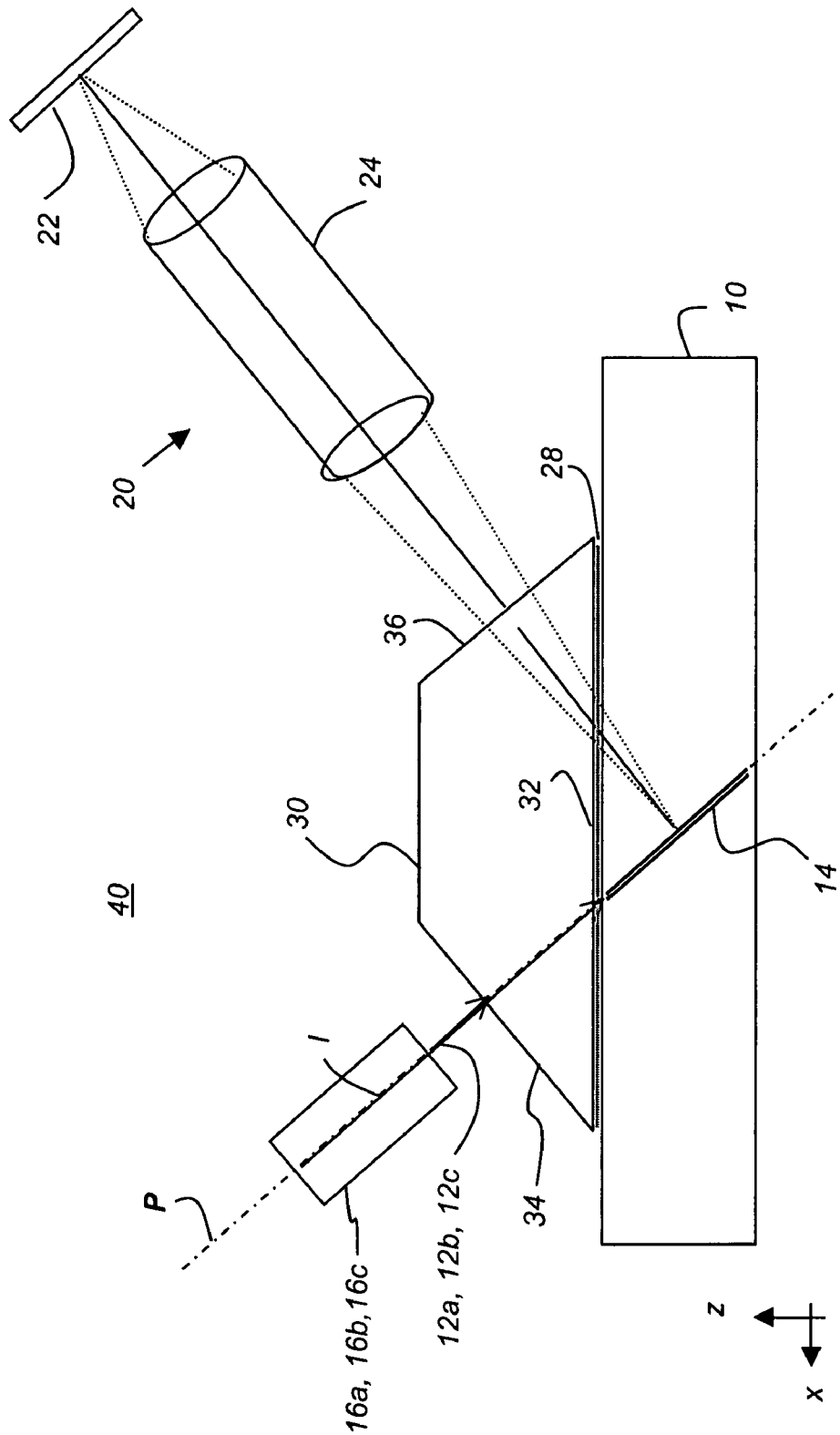
FIG. 8B is a side view of the embodiment shown in FIG. 8A.

Some types of inclusions, particularly those having a needle-like shape and oriented toward the light source, can be difficult to detect using scattered light from a single source. The perspective view of FIG. 8A shows an embodiment of optical apparatus 40 using multiple light sources 16a, 16b, and 16c providing corresponding ribbons of light 12a, 12b, and 12c. Light sources 16a, 16b, and 16c are fanned out at different angles. Here, light sources 16a, 16b, and 16c are coplanar, all directing their light within in the same plane P that includes primary illumination axis I, as shown in the side view of FIG. 8B. As the plan view of plane P in FIG. 8C shows, there is no refraction of ribbon of light 12b and some refraction of ribbons of light 12a and 12c. The intersection of ribbons of light 12a, 12b, and 12c within the volume of substrate 10 provides the illumination volume that corresponds to inspection volume 14. Light from multiple sources that are at relatively more extreme angles than those shown in FIGS. 8A and 8C could be used, provided that the illumination is along primary illumination axis I and properly coupled using index-matched coupler 30.

Adjustment for Varying Depths

The sequence of FIGS. 1A-1C showed how the apparatus of the present invention can scan through the volume of transparent substrate 10 in x- and y-axis directions. In addition to this capability, the method and apparatus of the present invention also have the capability to alter the scan depth.

Figure 9A:
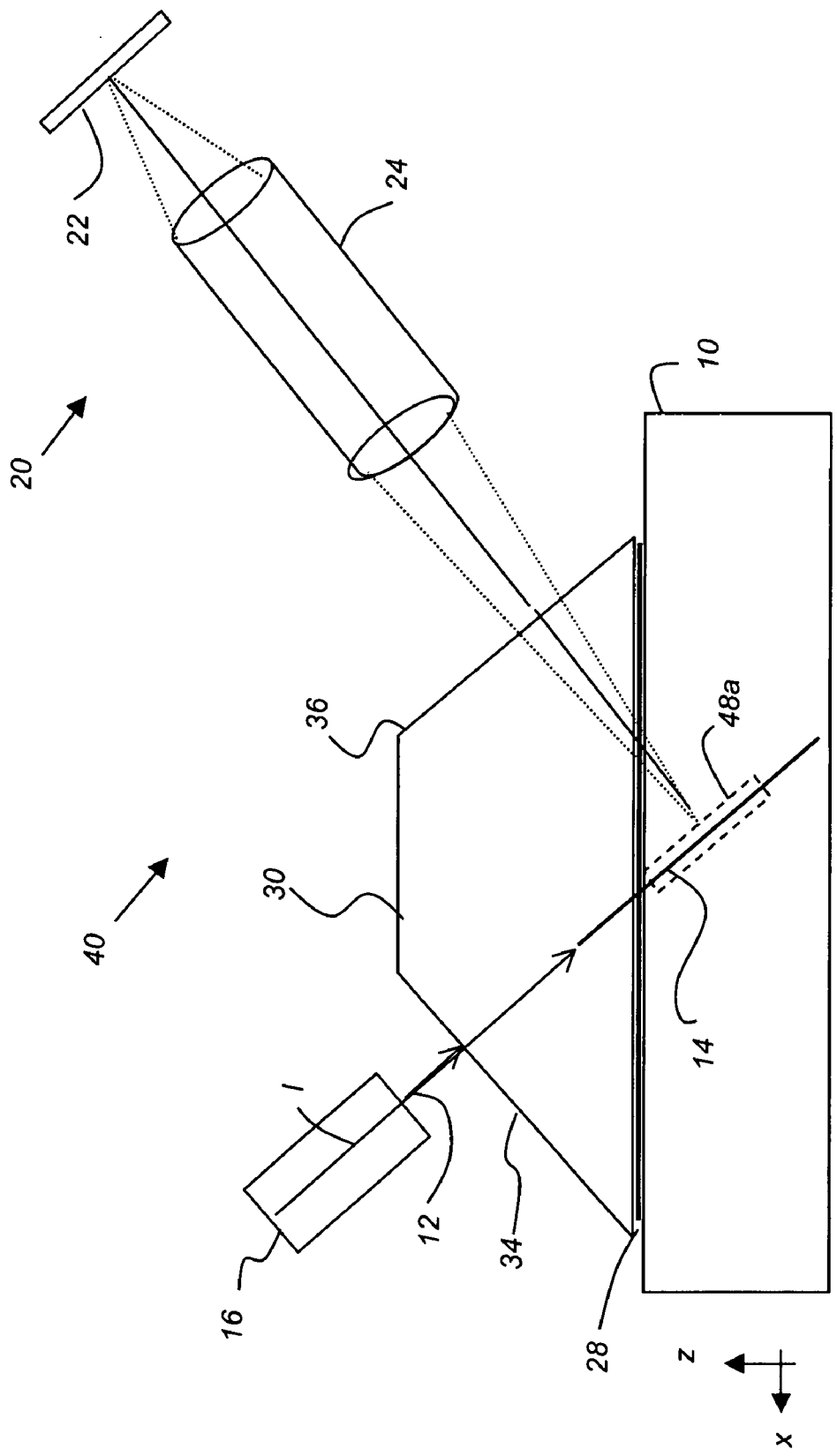
FIGS. 9A and 9B show how movement of detector apparatus components can be used to effect scanning at different depths within the transparent substrate.
Figure 9B:
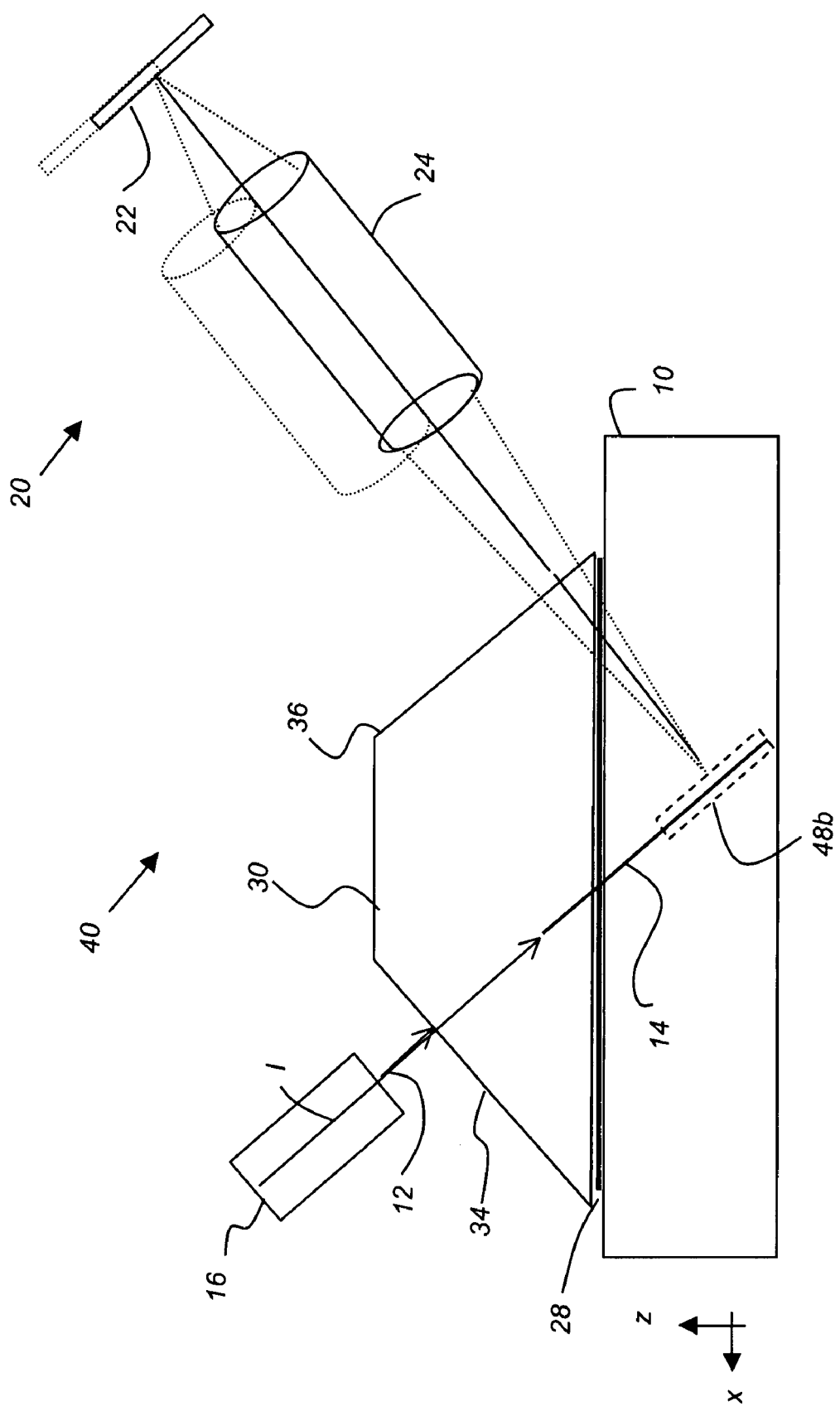

Referring to FIGS. 9A and 9B, there are shown side views with detector apparatus 20 movable for imaging over two positions, 48a and 48b, respectively, and thus capable of imaging inspection volume 14 at two different depths. As shown in phantom in FIG. 9B, this adjustment for depth simply translates detector apparatus 20 over short distance in the x-z plane and in a direction generally parallel to surface 36, maintaining the needed distance to surface 36 at each position. Using this capability, a volume of glass or other transparent substrate 10 of variable thickness can be examined. Thus, with the present invention, optical components of detector apparatus 20 do not need to be scaled up in size in order to inspect incrementally thicker substrates. Any of a number of types of actuator could be used to provide the needed translation of detector apparatus 20 components. This translation could also be performed by the transport apparatus. Alternately, manual adjustment of this position could be used.

Figure 10A:
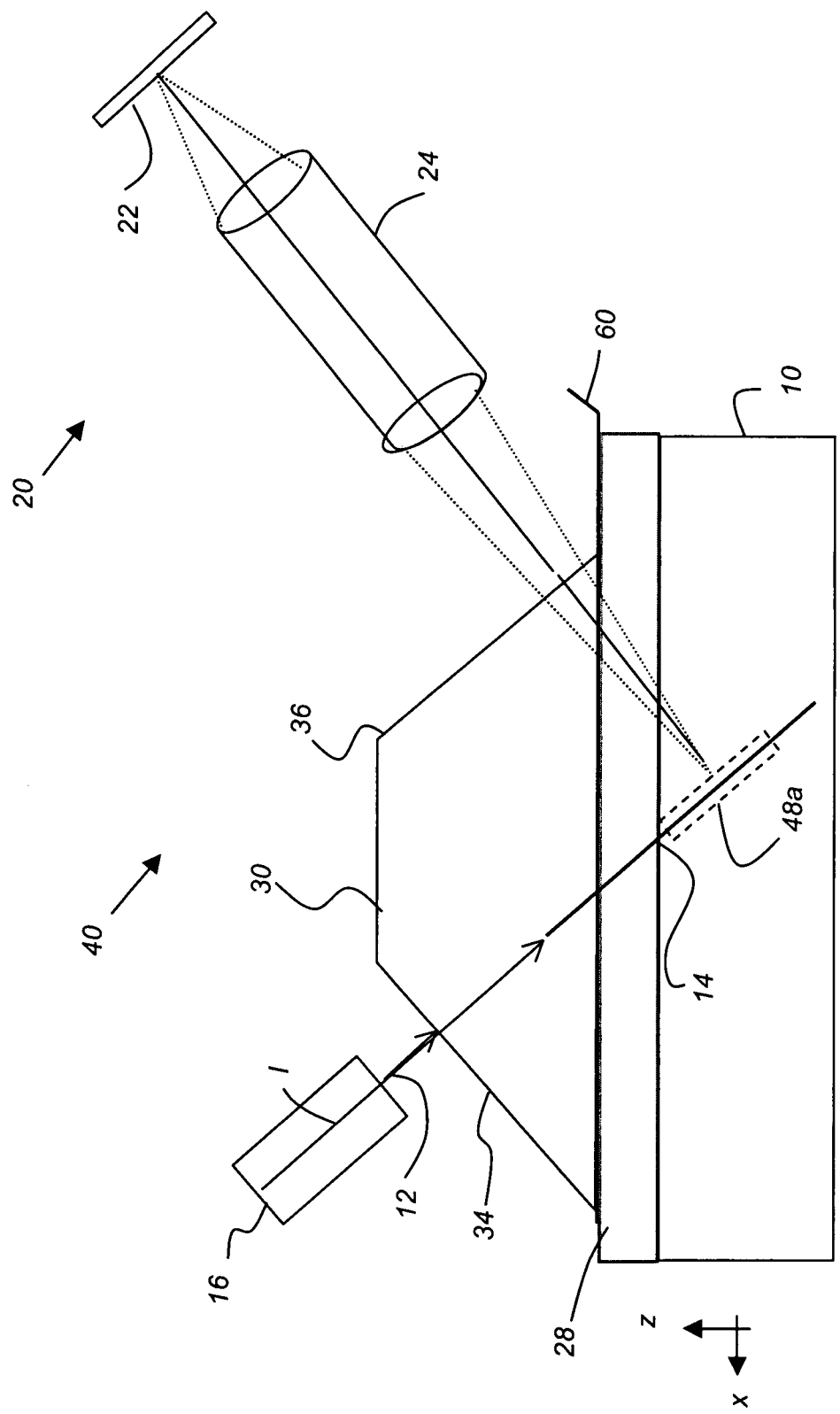
FIGS. 10A and 10B show another method that can be used to effect scanning at different depths within the transparent substrate.
Figure 10B:
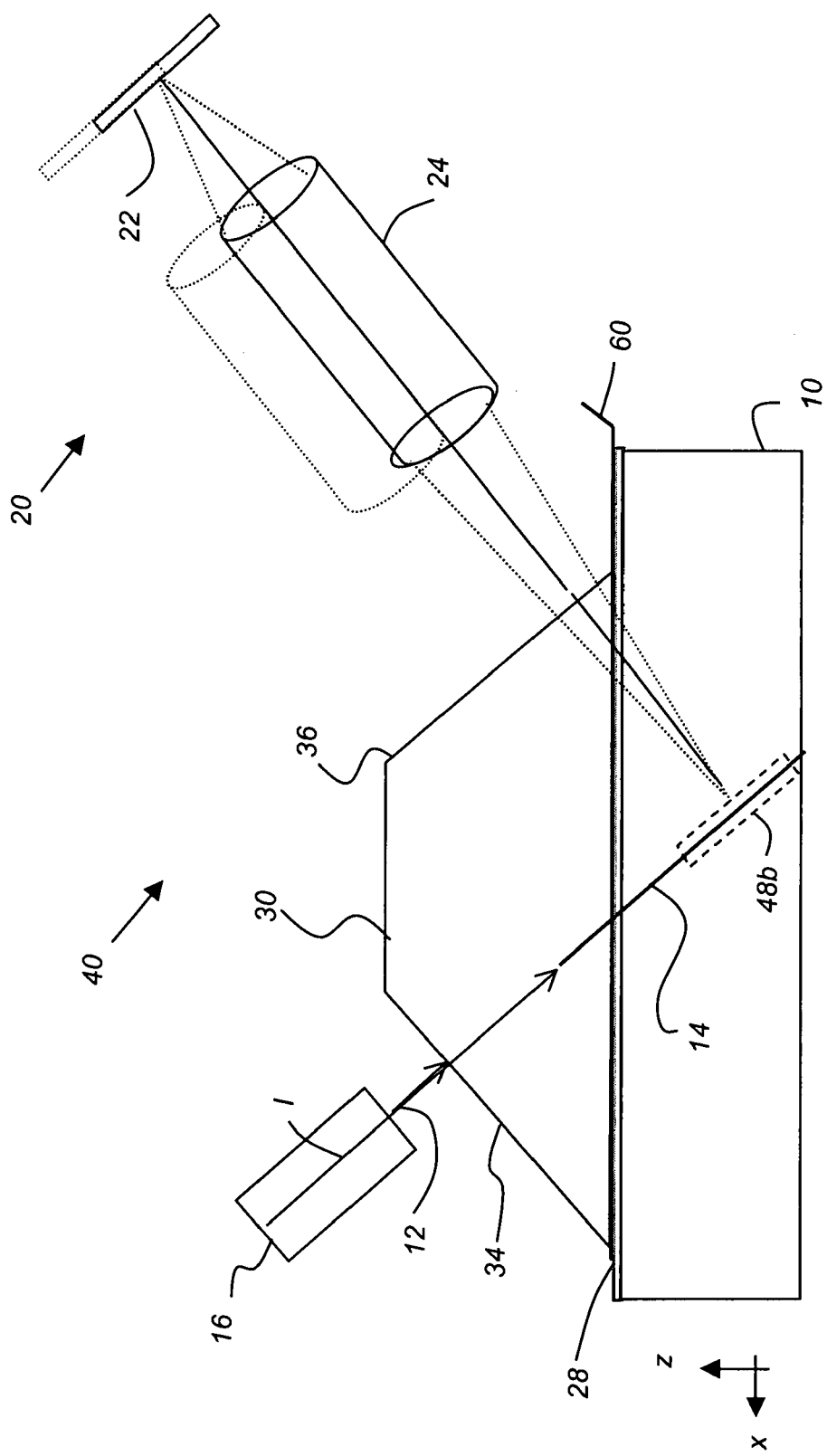

FIGS. 10A and 10B show an alternate embodiment for depth adjustment, varying the thickness of index-matching fluid 28 that lies between index-matched coupler 30 and the surface of substrate 10. The height of substrate 10 could be adjusted upward or downward, as shown. Alternately, a coupler support 60 can be used to lower index-matched coupler 30 into index-matching fluid 28. As yet another alternative, the combined coupler 30, detector apparatus 20, and light source 16 can be lowered into index-matching fluid 28. This effectively reduces the size of coupler surfaces 34 and 36.

Figure 16A:
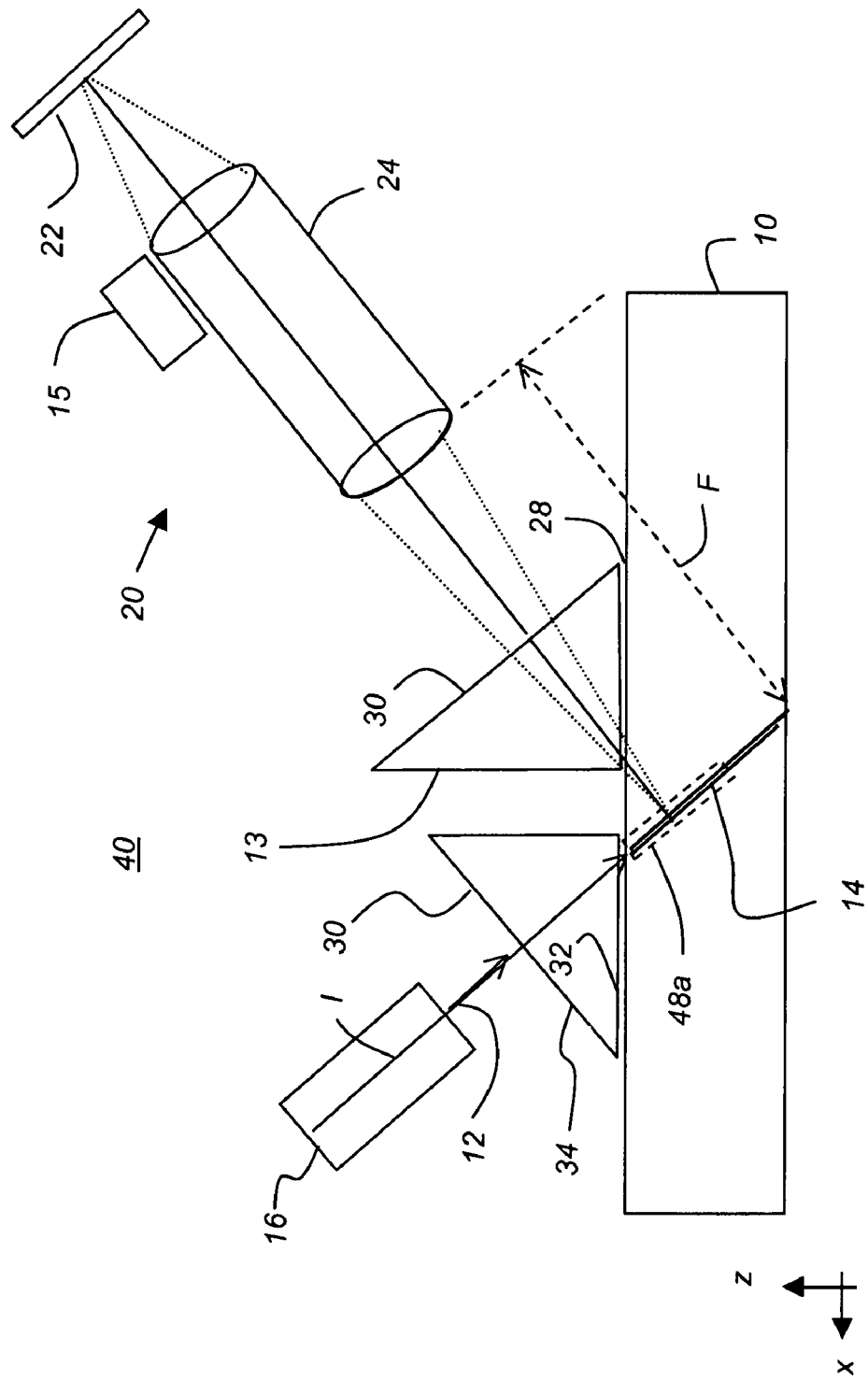
FIGS. 16A and 16B are side views showing an alternative embodiment for inspection of the transparent substrate at different depths.
Figure 16B:
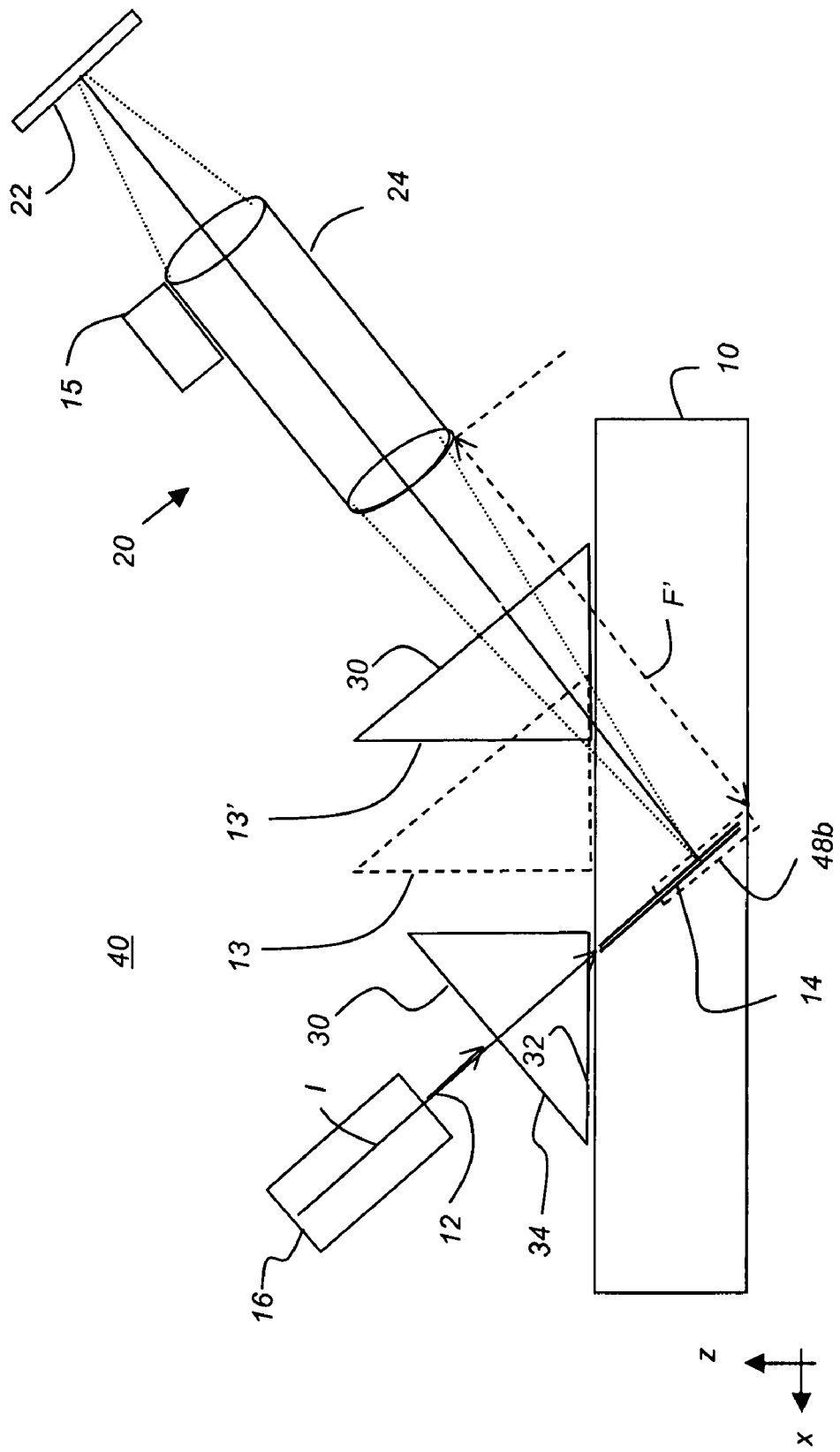

FIGS. 16A and 16B show yet another alternate embodiment that allows depth adjustment. Here, index-matched coupler 30 in the detection path can be moved along with its detector apparatus 20, while inspection volume 14 remains stationary. FIG. 16A shows this arrangement used to inspect depths at upper position 48a, with index-matched coupler 30 at a first position 13 and with a focal length F. FIG. 16B shows how movement to another position 13' and adjustment to a different focal length F' allows inspection at a lower depth position 48b. An actuator 15 allows change of focal length F; alternately, manual adjustment of focus could be used.

Embodiment Using Revisit Characterization Instrument

Figure 11:
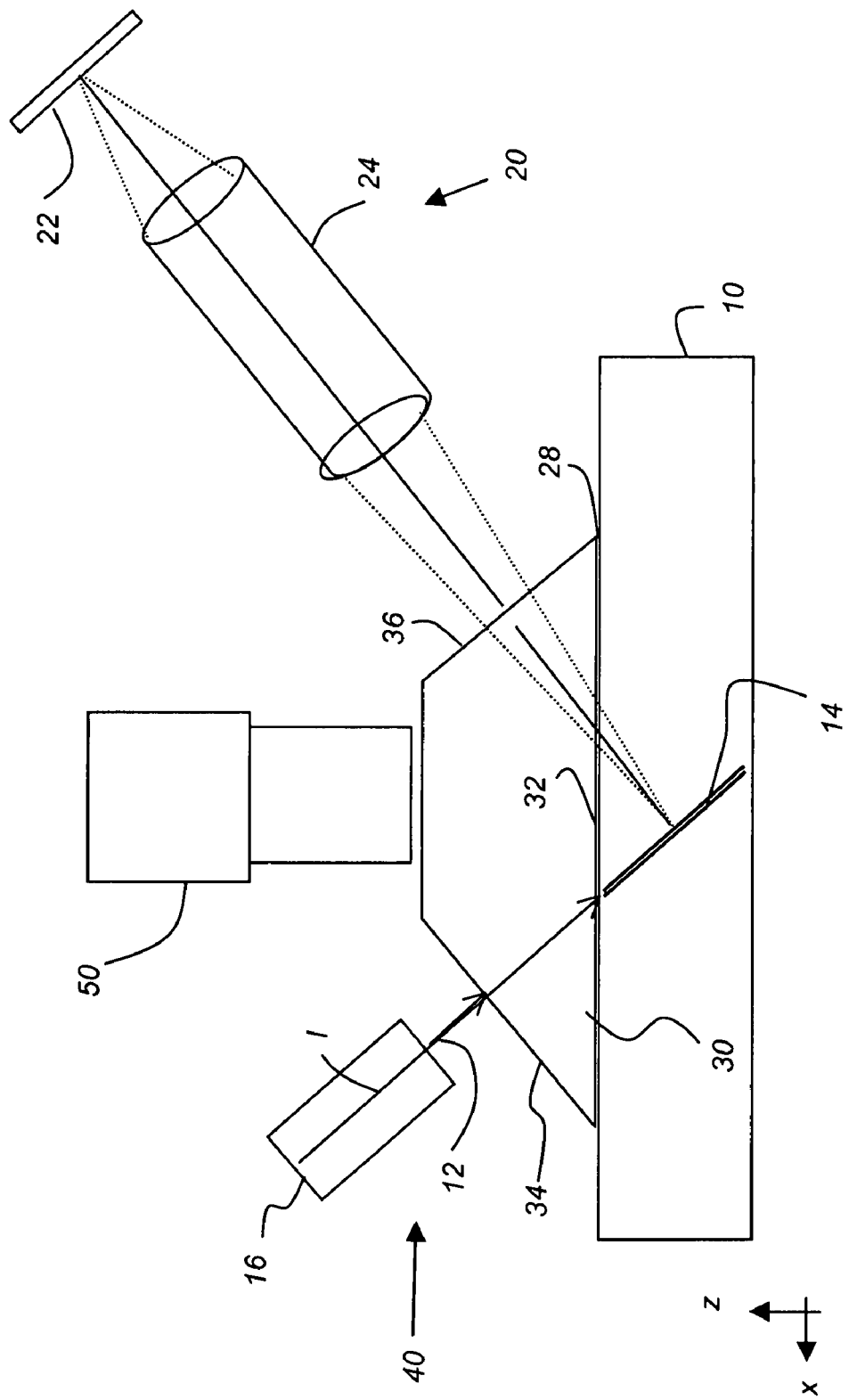
FIG. 11 is a cross-sectional schematic diagram showing an optical apparatus for inspection that includes a microscope or other revisit characterization instrument used for revisiting the site of a detected inclusion for closer inspection.

As shown in the side view of FIG. 11, a revisit characterization instrument 50, such as a microscope, or a camera or other inspection device, can be incorporated with optical apparatus 40. Using the arrangement shown in FIG. 11, detector apparatus 20 can be used for first determining the location of an inclusion. Then, close inspection of the location can be done using revisit characterization instrument 50. Revisit characterization instrument 50 can be a polarization scope, a Fourier Transform Infrared (FTIR) spectrometer, or some other suitable inspection device. Supporting illumination such as ring lighting can also be provided.

Figure 12:
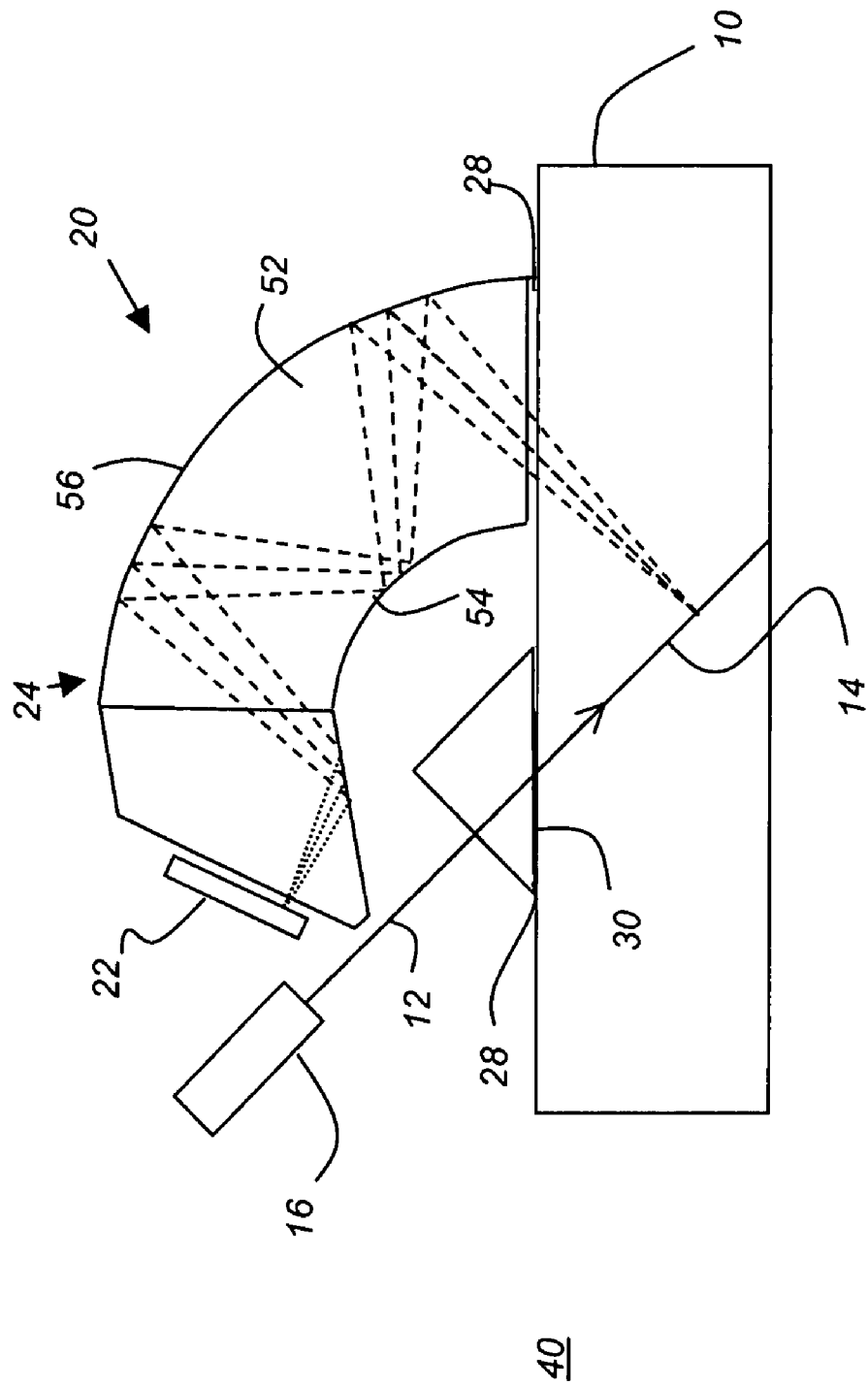
FIG. 12 is a cross-sectional schematic diagram showing a non-radially symmetric light director in one embodiment.
Figure 13:
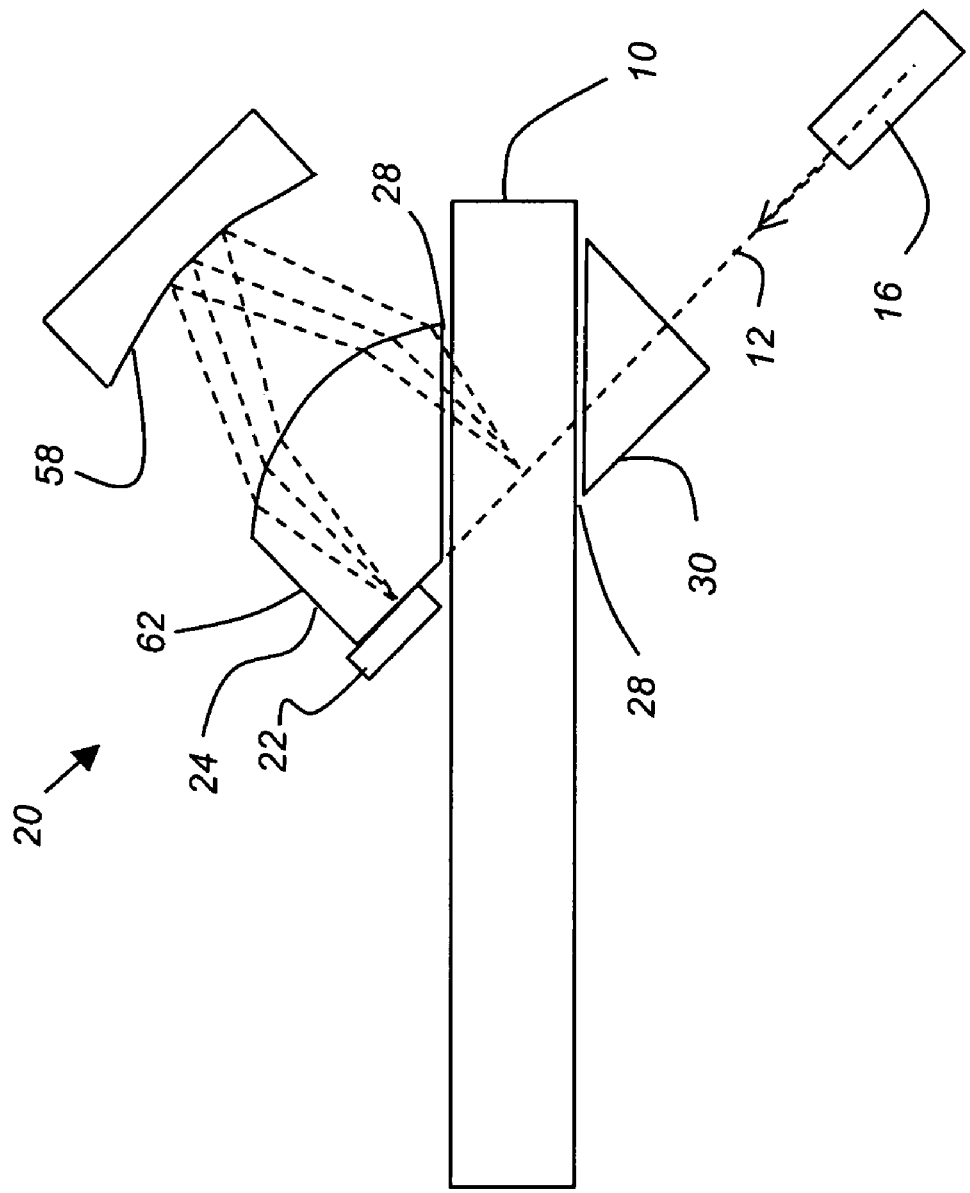
FIG. 13 is a cross-sectional schematic diagram showing a non-radially symmetric light director in another embodiment.

The present invention allows the use of a number of different optical configurations for light director 24 of detector apparatus 20, including embodiments that are not radially symmetric. The schematic side views of FIGS. 12 and 13 show two alternate arrangements of optical apparatus 40, by way of example. Referring first to FIG. 12, an index-matched optical coupler 52 is in optical contact with the surface of transparent substrate 10 using index-matching fluid 28. Optical coupler 52 has a pair of spherical reflective surfaces 54 and 56 that have the same center of curvature, using advantages of this optical arrangement as disclosed in U.S. Pat. No. 3,748,015 entitled "Unit Power Imaging Catoptric Anastigmat" to Offner. The optical path for light from illumination volume through optical coupler 52 is traced in dashed lines in FIG. 12. This arrangement has an advantage in being achromatic, allowing different wavelengths to be used, provided index-matching is maintained. FIG. 13 shows another embodiment that uses a combination of an index-matched optical coupler 62 and accompanying reflective surface 58. Here, illumination from light source 16 is directed from the bottom surface of transparent substrate 10. The optical path for output light to detector 22 can be folded within optical coupler 62. The basic optical path for detected light is again shown in dashed lines in FIG. 13.

Figure 14:
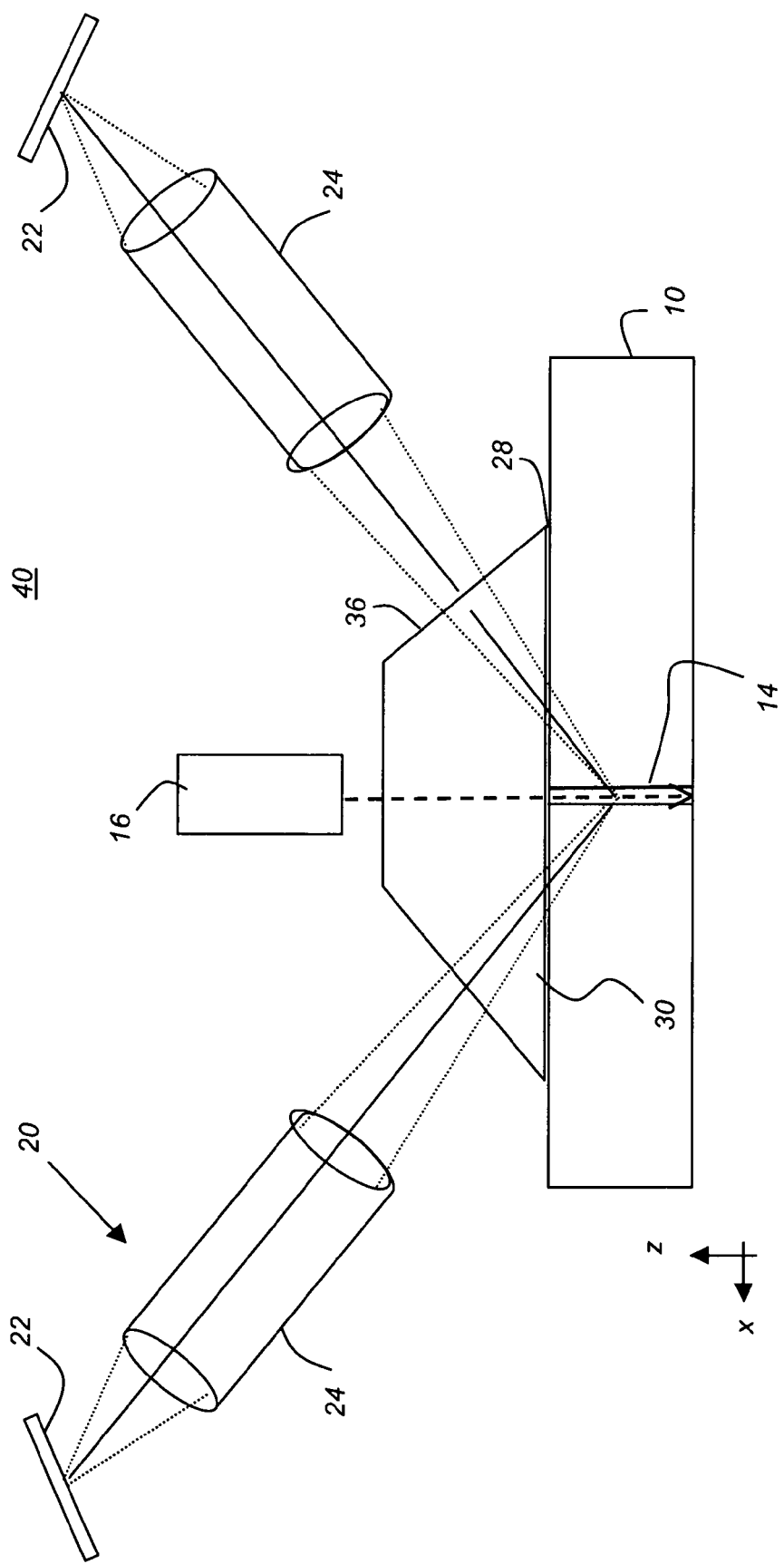
FIG. 14 is a cross-sectional schematic diagram showing an embodiment of the optical apparatus in which an inspection volume is formed perpendicular to the surface.

While there are advantages to forming inspection volume 14 at an oblique angle with respect to the surface of substrate 10, as shown in embodiments of FIGS. 1A through 13, it may alternately be desired to form inspection volume 14 normal to the surface. FIG. 14 shows an embodiment in which inspection volume 14 is formed at a normal or non-oblique angle. Two detectors 22 are used to obtain scattered light through their respective light directors 24; optionally, a single detector 22 and light director 24 could be used. Note that compensation for Scheimpflug distortion, caused by non-parallel lens and image planes, can be provided in this optical configuration by adjusting the angular orientation of each detector 22.

Figure 15:
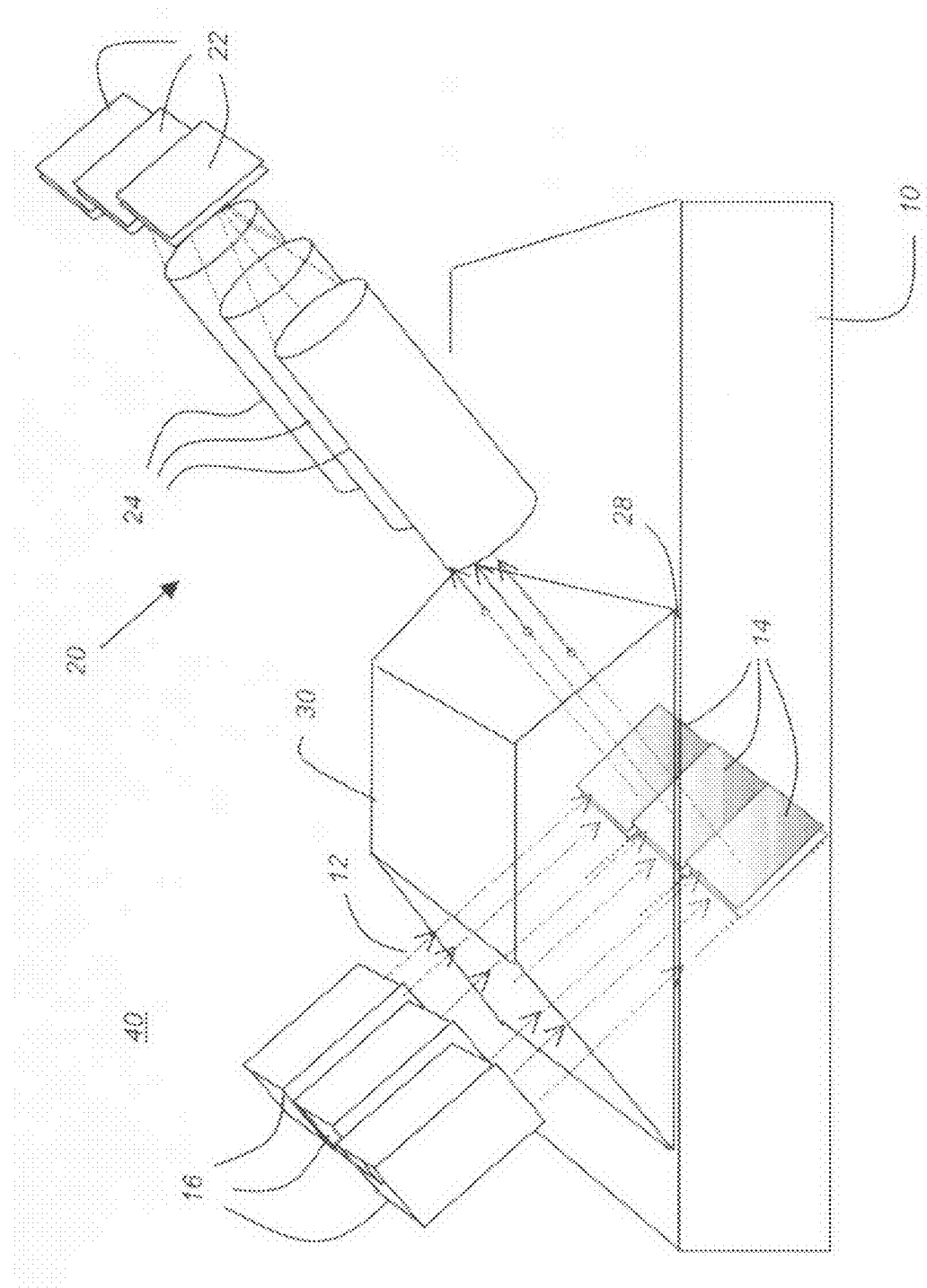
FIG. 15 is a perspective view of the optical apparatus using a set of multiple light directors and detectors in a detector apparatus according to one embodiment.

Yet other embodiments of the present invention use combinations in which detector apparatus 20 has more than one light director 24 and detector 22. The perspective view of FIG. 15 shows one inspection system embodiment that expands the scanned volume by placing two or more light directors 24 side-by-side. Each light director 24 and detector 22 can have a dedicated light source 16; alternately, a single light source 16 may provide one ribbon of light 12 that serves for each light director 24 in detector apparatus 20. Multiple optical couplers 30 or a single optical coupler 30, as shown in FIG. 15, could be used. In a similar arrangement (not shown), two or more light directors 24 could be used in detector apparatus 20, disposed to have inspection volumes 14 at different depths in transparent substrate 10.

It can be appreciated that the method and apparatus of the present invention can be adapted for inspecting the bulk material in a body of glass, plastic, or other transparent materials of variable thickness. Unlike conventional inspection methods, finishing and/or polishing of the substrate surface is not required for inspection of the material that lies beneath the surface. In practice, this means that the inspection of the substrate for inclusion defects can be carried out earlier in the fabrication cycle, reducing time and effort that might otherwise be wasted in finishing a defective piece of material. The apparatus and method of the present invention allow accurate detection of inclusions having dimensions in the micron range with a glass surface ground as coarsely as 120 grit. One advantage of the present invention relates to the ability to scan the inner volume of the substrate at a predetermined depth. In some cases of glass manufacture, for example, parts of the glass nearest the surface are of little interest for inspection, since the finishing process removes this portion of the material. The present invention allows inspection of usable portions of the material, with minimal interaction with unusable parts of the substrate such as near-surface regions. Yet another advantage relates to the ability to locate inclusions accurately. This helps to improve material yields by allowing a more efficient sectioning of final parts from a larger block of substrate.

Significantly, the present invention can be used with large sized substrates. Its adaptability to a number of different types of transport apparatus enables flexible application of the method and apparatus of the present invention and allows its use in a variety of substrate manufacture environments.

The apparatus of the present invention can be readily adapted to inspection of different types of glass. Coupling components and index-matching fluid would be changed for equipping the inspection apparatus of the present invention to be used with a different glass type. In addition, the apparatus and method can be used under a number of existing inspection conditions. This method is compatible with the use of immersion tanks filled with index-matching fluid, for example. Standard practices for providing light-absorbing surfaces around the glass or other substrate that is being inspected help to reduce stray light effects, as noted earlier.

A number of alterations are possible to the basic configuration of the present invention without departing from the scope of the invention. For example, while light source 16 may provide visible light, radiant energy from other parts of the electromagnetic spectrum could alternately be used. Inspection volume 14 could be formed using a ribbon of electromagnetic radiation of any suitable type, when combined with the appropriate coupling, index-matching, and detection elements.

Thus, what is provided is an apparatus and method for inspection of the bulk of a transparent substrate without the requirement for a finished surface.

The invention claimed is:

1. A method for inspecting a transparent substrate comprising:
   a) providing an index-matching fluid between an index-matched optical coupler and a surface of the transparent substrate; and
   b) repeating the following steps at two or more positions along the surface of the transparent substrate:
      (i) illuminating an inspection volume within the transparent substrate by directing a ribbon of light through the optical coupler and into the transparent substrate; and
      (ii) detecting scattered light from the inspection volume through the index-matched optical coupler at a detector that is optically conjugate with the inspection volume.

2. The method of claim 1 wherein directing the ribbon of light comprises scanning a laser beam in a predetermined pattern.

3. The method of claim 1 wherein directing the ribbon of light comprises directing a beam of light through a holographic diffuser.

4. The method of claim 1 wherein directing the ribbon of light comprises actuating a light source taken from the group consisting of a laser, a light-emitting diode, a strobed light source, and a lamp.

5. The method of claim 1 wherein, when at a first position along the surface of the transparent substrate, the detector is optically conjugate to the inspection volume at a first depth from the surface of the substrate and wherein, when at a second position along the surface of the transparent substrate, the detector is optically conjugate to the inspection volume at a second depth from the surface of the substrate.

6. The method of claim 1 further comprising adjusting the level of the inspection volume by varying the depth of the index-matching fluid between the surface of the index matched optical coupler and the surface of the transparent substrate.

7. The method of claim 1 wherein illuminating the inspection volume comprises providing polarized light.

8. The method of claim 1 wherein the transparent substrate is glass.

9. The method of claim 1 further comprising moving the transparent substrate in order to move between positions.

10. The method of claim 1 further comprising moving the index-matched optical coupler and the detector to move between positions.

11. The method of claim 1 wherein directing the ribbon of light through the optical coupler and into the transparent substrate comprises directing light from two or more light sources along the same principal illumination axis.

12. The method of claim 1 wherein directing the ribbon of light comprises directing light that is at an oblique angle to the surface of the transparent substrate.

13. The method of claim 1 wherein directing the ribbon of light comprises directing visible light.

14. The method of claim 1 wherein directing the ribbon of light comprises directing light that is outside the visible spectrum.

15. The method of claim 1 wherein directing the ribbon of light comprises directing monochromatic light.

16. An apparatus for inspecting a transparent substrate comprising:
(a) an optical apparatus comprising:
(i) at least one light source disposed to direct a ribbon of light toward the substrate along a principal illumination direction;
(ii) at least one detector apparatus comprising a detector and a light director that is disposed to direct light scattered from the ribbon of light along an optical path toward the detector;
(iii) an index-matched optical coupler that is disposed to direct the ribbon of light into, and the scattered light out from, the transparent substrate, the index-matched optical coupler having a first surface substantially normal to the principal illumination direction, having a second surface substantially normal to the optical path of the light director, and having a third surface, and having an index of refraction n equal to the index of refraction of the transparent substrate;
(b) an index-matching fluid having the index of refraction n and providing optical contact between the third surface of the index-matched optical coupler and a surface of the transparent substrate; and
(c) a transport apparatus actuable to provide relative motion between the optical apparatus and the transparent substrate.

17. The apparatus of claim 16 wherein the at least one light source, at least one detector apparatus, and the index-matched optical coupler of the optical apparatus are mechanically coupled.

18. The apparatus of claim 16 wherein the transport apparatus further moves the at least one detector apparatus in a direction that is parallel to the second surface of the index-matched optical coupler.

19. The apparatus of claim 16 wherein the light director comprises two or more curved reflective surfaces.

20. The apparatus of claim 16 wherein the light director comprises at least one refractive element and at least one curved reflective surface.

21. The apparatus of claim 16 wherein the optical apparatus further comprises one or more polarizer elements.

22. The apparatus of claim 16 wherein the detector apparatus further comprises a polarized light analyzer.

23. The apparatus of claim 16 wherein the first surface of the optical coupler comprises a curved refractive surface.

24. The apparatus of claim 16 wherein the second surface of the optical coupler comprises a curved refractive surface.

25. The apparatus of claim 16 wherein the optical apparatus further comprises a characterization instrument for close inspection.

26. The apparatus of claim 25 wherein the characterization instrument is a microscope.

27. The apparatus of claim 16 wherein the index-matched optical coupler is a prism.

28. The apparatus of claim 16 wherein the detector is taken from the group consisting of a photodetector, a charge-coupled detector, and a CMOS detector.

29. The apparatus of claim 16 further comprising a conduit for supplying the index-matching fluid between the optical coupler and the transparent substrate, wherein the conduit is coupled to the optical coupler.

30. The apparatus of claim 16 wherein the light detector is radially symmetric about the optical path.

31. The method of claim 16 further comprising an actuator for translating the at least one detector apparatus in a direction that is substantially parallel to the second surface of the optical coupler.

32. The apparatus of claim 16 wherein the substrate is disposed within a container of index-matching fluid.

33. The apparatus of claim 16 wherein at least a portion of the third surface of the index-matched optical coupler is treated to reduce detection of unwanted scattered light.

34. The apparatus of claim 16 wherein multiple light sources are used and all of the light sources direct their corresponding ribbons of light in the principal illumination direction and substantially within the same plane.

35. An apparatus for inspecting a transparent substrate comprising:
(a) at least one optical apparatus comprising:
(i) at least one light source disposed to direct a ribbon of light toward the substrate along a principal illumination direction;
(ii) at least one detector apparatus comprising a detector and a light director disposed to direct light scattered from the ribbon of light along an optical path toward the detector;
(iii) a first optical coupler disposed to direct the ribbon of light into the transparent substrate, having a first surface substantially normal to the principal illumination direction, having a second surface, and having an index of refraction n equal to the index of refraction of the transparent substrate;
(iv) a second optical coupler disposed to direct the scattered light out from the transparent substrate and toward the at least one detector, the second optical coupler having a third surface substantially normal to the optical path of the light director, having a fourth surface, and having index of refraction n;
(b) an index-matching fluid having the index of refraction n and providing optical contact between the second surface of the first optical coupler and the transparent substrate and between the fourth surface of the second optical coupler and the transparent substrate; and
(c) a transport apparatus actuable to provide relative motion between the at least one optical apparatus and the transparent substrate.

36. The apparatus of claim 35 wherein the first and second optical couplers are on the same side of the transparent substrate.

37. The apparatus of claim 35 wherein the first and second optical couplers are on opposite sides of the transparent substrate.

38. The apparatus of claim 35 wherein the light source, detector apparatus, first optical coupler, and second optical coupler of the optical apparatus are mechanically coupled with respect to motion caused by actuation of the transport apparatus.

39. The apparatus of claim 35 wherein the second optical coupler further comprises at least one curved reflective surface.

40. The apparatus of claim 35 further comprising an actuator for adjusting the focal length of the light director.

41. The apparatus of claim 35 wherein the detector is in communication with an automated image analysis system.

42. The apparatus of claim 35 wherein the second optical coupler can be moved along the surface of the substrate, independently of the first optical coupler.

* * * * *